(12) United States Patent
Nishihara et al.

(10) Patent No.: US 11,313,980 B2
(45) Date of Patent: Apr. 26, 2022

(54) RADIATION DETECTION APPARATUS

(71) Applicant: SONY SEMICONDUCTOR SOLUTIONS CORPORATION, Kanagawa (JP)

(72) Inventors: Toshiyuki Nishihara, Kanagawa (JP); Tsutomu Imoto, Kanagawa (JP); Masao Matsumura, Kanagawa (JP); Hiroyasu Baba, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 83 days.

(21) Appl. No.: 16/631,538

(22) PCT Filed: Jul. 11, 2018

(86) PCT No.: PCT/JP2018/026142
§ 371 (c)(1),
(2) Date: Jan. 16, 2020

(87) PCT Pub. No.: WO2019/021819
PCT Pub. Date: Jan. 31, 2019

(65) Prior Publication Data
US 2020/0200923 A1    Jun. 25, 2020

(30) Foreign Application Priority Data

Jul. 25, 2017  (JP) .............................. JP2017-143262
Jun. 4, 2018   (JP) .............................. JP2018-106857

(51) Int. Cl.
*G01T 1/20*    (2006.01)
*G06T 11/00*   (2006.01)
(Continued)

(52) U.S. Cl.
CPC .......... *G01T 1/2002* (2013.01); *G01T 1/1663* (2013.01); *G06T 11/003* (2013.01); *A61B 6/03* (2013.01)

(58) Field of Classification Search
None
See application file for complete search history.

(56) References Cited

U.S. PATENT DOCUMENTS

| 5,525,803 A | 6/1996 | Watanabe et al. |
| 6,545,624 B2 * | 4/2003 | Lee ........................ H04N 5/378 341/155 |

(Continued)

FOREIGN PATENT DOCUMENTS

| JP | 07-049386 A | 2/1995 |
| JP | 2002-022678 A | 1/2002 |

(Continued)

OTHER PUBLICATIONS

Nishihara, et al., "An Experimental CMOS Photon Detector with 0.5e- RMS Temporal Noise and 15μm pitch Active Sensor Pixels", International Electron Devices Meeting (IEDM), IEEE, Jan. 25, 2018, 04 pages.

(Continued)

*Primary Examiner* — Edwin C Gunberg
(74) *Attorney, Agent, or Firm* — Chip Law Group

(57) ABSTRACT

The present technology relates to a radiation detection apparatus that makes it possible to obtain a projection image of a radiation in a short period of time. The radiation detection apparatus includes a scintillator that emits scintillation light in response to incidence of a radiation, a pixel substrate on which a plurality of pixels each of which photoelectrically converts the scintillation light and outputs a pixel signal according to a light amount of the scintillation light is disposed in an array, a detection circuit substrate that includes an A/D (Analog to Digital) conversion unit for A/D (Continued)

converting the pixel signal and is stacked on the pixel substrate, and a compression unit that compresses digital data outputted from the A/D conversion unit. The present technology can be applied, for example, to an X-ray imaging apparatus that detects an X-ray to perform imaging and so forth.

15 Claims, 19 Drawing Sheets

(51) Int. Cl.
  *G01T 1/166* (2006.01)
  *A61B 6/03* (2006.01)

(56) References Cited

U.S. PATENT DOCUMENTS

| | | | | |
|---|---|---|---|---|
| 2002/0153492 | A1* | 10/2002 | Sekine | .................. G01T 1/2018 250/370.11 |
| 2004/0013224 | A1 | 1/2004 | Baba et al. | |
| 2006/0039527 | A1 | 2/2006 | Malamud | |
| 2010/0142811 | A1* | 6/2010 | Okamoto | .................. H04N 1/41 382/166 |
| 2015/0285921 | A1* | 10/2015 | Shah | ....................... G01T 1/208 600/411 |

FOREIGN PATENT DOCUMENTS

| | | |
|---|---|---|
| JP | 2005-537846 A | 12/2005 |
| JP | 2017-020912 A | 1/2017 |
| WO | 2006/101230 A1 | 9/2006 |

OTHER PUBLICATIONS

International Search Report and Written Opinion of PCT Application No. PCT/JP2018/026142, dated Aug. 21, 2018, 09 pages of ISRWO.

Nishihara, et al., "An experimental CMOS photon detector with 0.5e-RMS temporal noise and 15μm pitch active sensor pixels", IEEE International Electron Devices Meeting (IEDM), Jan. 25, 2018, 04 pages.

* cited by examiner

TO DETECTION CIRCUIT

RADIATION DETECTION APPARATUS

CROSS REFERENCE TO RELATED APPLICATIONS

This application is a U.S. National Phase of International Patent Application No. PCT/JP2018/026142 filed on Jul. 11, 2018, which claims priority benefit of Japanese Patent Application No. JP 2018-106857 filed in the Japan Patent Office on Jun. 4, 2018 and also claims priority benefit of Japanese Patent Application No. JP 2017-143262 filed in the Japan Patent Office on Jul. 25, 2017. Each of the above-referenced applications is hereby incorporated herein by reference in its entirety.

TECHNICAL FIELD

The present technology relates to a radiation detection apparatus, and particularly to a radiation detection apparatus that makes it possible to obtain a projection image of a radiation in a short period of time, for example.

BACKGROUND ART

There is proposed a photon counting type FPD (Flat Panel Detector) apparatus which detects X-ray photons individually one by one and counts the number of X-ray photons within a specific energy range for each pixel to generate an X-ray projection image (for example, PTL 1).

CITATION LIST

Patent Literature

[PTL 1]
Japanese Patent Laid-open No. 2017-020912

SUMMARY

Technical Problem

At present, it is demanded to obtain a projection image of a radiation in a short period of time.

The present technology has been made in view of such a situation as described above and makes it possible to obtain a projection image of a radiation in a short period of time.

Solution to Problem

The radiation detection apparatus of the present technology is a radiation detection apparatus including a scintillator that emits scintillation light in response to incidence of a radiation, a pixel substrate on which a plurality of pixels each of which photoelectrically converts the scintillation light and outputs a pixel signal according to a light amount of the scintillation light is disposed in an array, a detection circuit substrate that includes an A/D (Analog to Digital) conversion unit for A/D converting the pixel signal and is stacked on the pixel substrate, and a compression unit that compresses digital data outputted from the A/D conversion unit.

In the radiation detection apparatus of the present technology, the plurality of pixels that performs photoelectric conversion of the scintillation light and outputs a pixel signal corresponding to the light amount of the scintillation light is arranged in an array on the pixel substrate. The detection circuit substrate includes the A/D (Analog to Digital) conversion unit that performs A/D conversion for the pixel signal, and is stacked on the pixel substrate. Then, the digital data outputted from the A/D conversion unit is compressed by the compression unit.

It is to be noted that the radiation detection apparatus may be an independent apparatus or may otherwise be an internal block configuring one apparatus.

Advantageous Effect of Invention

With the present technology, a projection image of a radiation can be obtained in a short period of time.

It is to be noted that the effect described here is not necessarily limited and may be one of advantageous effects described in the present disclosure.

DESCRIPTION OF EMBODIMENT

Figure 1:
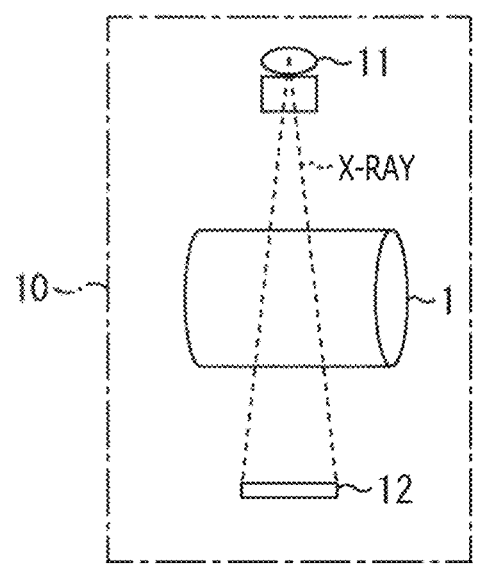
FIG. 1 is an overhead view depicting an example of a configuration of an embodiment of an X-ray imaging apparatus to which a radiation detection apparatus of the present technology is applied.

For example, in the medical field, an X-ray medical imaging apparatus that monitors a projection image projected by applying an X-ray, as a moving picture or a still picture, is utilized. The X-ray medical imaging apparatus includes an X-ray tube that is a generation unit of an X-ray and an FPD apparatus as a detection apparatus for an X-ray (X-ray detection apparatus) disposed at a position opposed to the X-ray tube with a subject interposed therebetween.

Together with dealing with decrease of radiation exposure, enhancement of picture quality of a projection image of the X-ray is demanded for the X-ray medical imaging apparatus. Further, the X-ray medical imaging apparatus sometimes includes a tomography function for capturing an image of a cross section (tomographic image) such as a cone beam CT (Computed Tomography) or a tomosynthesis, and, where the X-ray medical imaging apparatus has a tomographic function, the FPD apparatus is used as a detection apparatus for an X-ray.

In the FPD apparatus as a detection apparatus for an X-ray, a detection face for detecting an X-ray includes a scintillator plate that emits fluorescence light (scintillation light) in response to incidence of an X-ray and an array of pixels (pixel array) including a PD (Photodiode) that performs photoelectric conversion in response to light (here, scintillation light).

In each pixel of the FPD apparatus, scintillation light generated in response to irradiation of the scintillator plate with an X-ray is converted into charge by the PD. A pixel signal as an electric signal corresponding to the charge of the PD is read out by a reading out circuit that includes a pixel Tr (transistor) built in the pixel and is converted into a digital value by an A/D converter, and is then detected as an irradiation amount (transmission amount) of an X-ray.

Reading out of the pixel signal is performed, for example, in imaging for obtaining a projection image of a still picture, by one to several times, but is carried out, in imaging for obtaining a projection image of a moving picture, in a frequency of approximately 10 to 30 times in one second. In the FPD apparatus, charge corresponding to scintillation light by a great number of X-rays is accumulated integrally into the PD of each pixel and the pixel signal corresponding to the charge is read out for each pixel. Then, deeming that the pixel signal of each pixel changes in proportion to the light amount of a transmission X-ray that is an X-ray incident on the pixel and transmitted through a subject, a projection image is generated.

As described above, what is generally called an integration type FPD apparatus in which a pixel signal corresponding to charge accumulated integrally in a PD is read out to generate a projection image has a problem of accumulation of noise.

In particular, the light emission amount of a scintillator plate changes substantially in proportion to energy of an X-ray, and the scintillator plate itself has light emission dispersion. The energy of an X-ray emitted from an X-ray tube has a width of a spectrum, and dispersion of energy for each spectrum of the X-ray and light emission dispersion of the scintillator plate are generated every time the X-ray is incident. Then, the dispersion of energy of the X-ray and the light emission dispersion of the scintillator plate are accumulated as noise into the PD of the pixel. Noise originating from the sum of noise arising from the dispersion of energy of the X-ray and the light emission dispersion of the scintillator plate and readout noise generated from the pixel itself is reflected on a projection image, as noise of the pixel signal read out from the pixel.

Further, where the X-ray tube emits an X-ray having a wide energy spectrum, since the transmittance through a substance is different between a low-energy X-ray and a high-energy X-ray, a phenomenon called beam hardening in which blur of a projection image appears occurs due to the difference in transmittance.

Further, in a case where an X-ray from which position information is lost by dispersion is incident on an integration type FPD apparatus, the X-ray becomes noise to the projection image.

As an FPD apparatus that overcomes the problem of accumulation of noise occurring in such an integration type FPD apparatus as described above, there is proposed a photon counting type FPD apparatus in which photons of an X-ray are detected individually one by one and the number of photons of the X-ray within a specific energy range is counted for each pixel to generate a projection image of an X-ray.

Since it is necessary for the photon counting type FPD apparatus to capture weak signals generated by one photon of the X-ray, individually one by one, very high sensitivity and high-speed responsibility are required for a pixel. Therefore, in an attempt for implementing a photon counting type FPD apparatus, instead of indirect conversion in which an X-ray is converted indirectly into charge using a scintillator plate, direction conversion in which an X-ray is converted directly into charge using a special semiconductor material as typified by CdTe or CZT is presupposed.

For example, there is proposed a photon counting method in which CZT crystal detects charge generated by incidence of individual X-rays using a silicon detector disposed for each pixel in a lower layer of the CZT crystal and (a signal corresponding to) charge having a magnitude within a fixed range is counted by a counter while being compared with a threshold value by a comparator.

However, a semiconductor material such as CdTe or CZT is very expensive and has a problem in crystallinity, stability of crystal, and uniformity of crystal. Thus, manufacture of an FPD apparatus having a great area is difficult at present from a viewpoint of floor noise and instability of a state arising from the problem of crystallinity and so forth.

Further, where (a signal corresponding to) the charge is counted by a counter, a dynamic range of detection of an X-ray (dynamic range of a count value when photons of an X-ray are counted) is limited with a bit number of the counter. Generally, in tomography such as a cone beam CT or tomosynthesis in which a tomographic image is captured, it is necessary to capture a great number of projection images in a short period of time in comparison with two-dimensional transmission imaging for capturing a two-dimensional projection image and the dose of an X-ray increases significantly. Here, the dose of an X-ray signifies a frequency when an X-ray is applied or the number (density) of X-rays.

Where the dose of an X-ray is high, charge corresponding to the X-ray is generated not in a pulse form but continuously and constantly and it is difficult to count the charge.

Accordingly, it is difficult for a photon counting type FPD apparatus that counts charge by a counter to detect an X-ray having such a high dose as in the case where tomographic imaging is performed. In such a photon counting type FPD apparatus as just described, in order to cope with an X-ray having a high dose, it is expected that a circuit for detecting a high-dose X-ray is incorporated for each pixel separately from a photon counting type circuit and is used in a switchable manner. However, this increases the cost of the FPD apparatus.

Therefore, the present technology makes it possible to detect both a radiation ray having a high dose used for tomographic imaging or the like and a radiation ray having a low dose used for two-dimensional transmission imaging or the like with a low cost.

<Embodiment of X-Ray Imaging Apparatus to which Present Technology is Applied>

FIG. 1 is an overhead view depicting an example of a configuration of an embodiment of an X-ray imaging apparatus to which the radiation detection apparatus of the present technology is applied.

Referring to FIG. 1, the X-ray imaging apparatus 10 includes an X-ray irradiation apparatus 11 and the detection apparatus 12.

The X-ray irradiation apparatus 11 and the detection apparatus 12 are arranged in an opposing relationship to each other sandwiching a subject 1 therebetween.

The X-ray irradiation apparatus 11 is a radiation generation unit that generates an X-ray that is one of radiations and irradiates the subject 1 with an X-ray.

The detection apparatus 12 is, for example, an FPD apparatus that detects an X-ray, and detects (photons of) an X-ray generated by the X-ray irradiation apparatus 11 and transmitted through the subject 1, and then generates a two-dimensional projection image corresponding to the X-ray.

The X-ray imaging apparatus 10 has, as imaging modes, a transmission imaging mode in which two-dimensional transmission imaging for capturing a two-dimensional projection image is performed and a tomography imaging mode in which tomographic imaging in which a great number of two-dimensional projection images are captured and a tomographic image is acquired from the great number of projection images is performed.

FIGS. 2A, 2B, 2C, and 2D depict diagrams illustrating examples of a state of the X-ray imaging apparatus 10 in each of the cases of the transmission imaging mode and the tomography imaging mode.

Figure 2A:
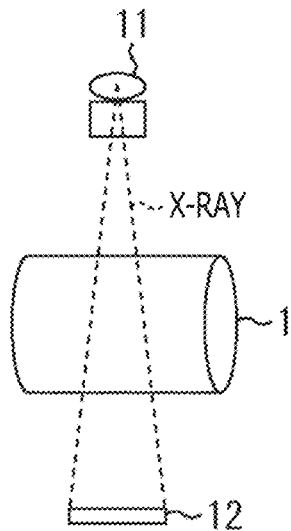
FIGS. 2A, 2B, 2C, and 2D depict diagrams illustrating examples of a state of an X-ray imaging apparatus 10 in each of cases of a transmission imaging mode and a fault imaging mode.

FIG. 2A depicts an example of a state of the X-ray imaging apparatus 10 in the transmission imaging mode. In FIG. 2A, the X-ray irradiation apparatus 11 and the detection apparatus 12 configuring the X-ray imaging apparatus 10 are fixed at predetermined positions sandwiching the subject 1 therebetween and a projection image of a partial range of the subject 1 is captured.

Figure 2B:
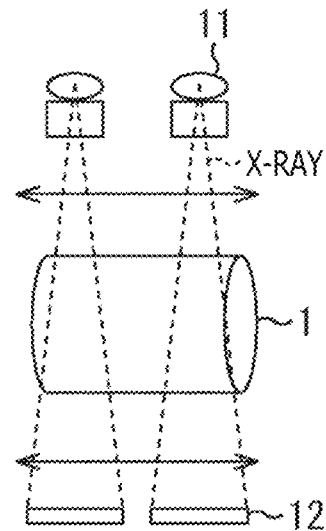

FIG. 2B depicts a different example of a state of the X-ray imaging apparatus 10 in the transmission imaging mode. In FIG. 2B, the X-ray irradiation apparatus 11 and the detection apparatus 12 configuring the X-ray imaging apparatus 10 capture a projection image over a wide range of the subject 1 while being slid in the same direction.

Figure 2C:
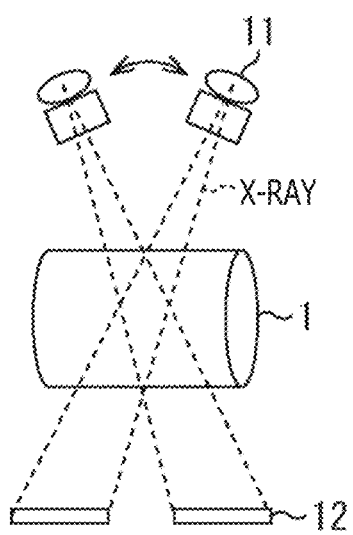

FIG. 2C depicts an example of a state of the X-ray imaging apparatus 10 in the tomographic imaging mode. In FIG. 2C, the X-ray irradiation apparatus 11 is moved so as to rotate around the subject 1 and the detection apparatus 12 is slid in a direction opposite to the moving direction of the X-ray irradiation apparatus 11.

Figure 2D:
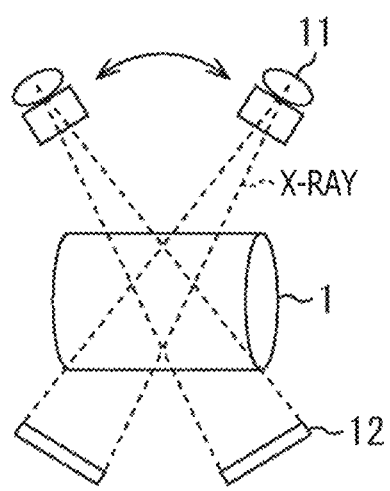

FIG. 2D depicts a different example of a state of the X-ray imaging apparatus 10 in the tomographic imaging mode. In FIG. 2D, the X-ray irradiation apparatus 11 and the detection apparatus 12 are integrally rotated around the subject 1.

In the tomographic imaging mode of FIGS. 2C and 2D, part of the subject 1 is imaged from a plurality of different angles to generate a plurality of projection images viewed from the plurality of different angles, and a three-dimensional tomographic image is generated from the plurality of projection images. In the tomographic imaging mode, it is necessary to capture a great number of projection images within a limited, fixed period of time and, for example, a high-dose X-ray is used for the capturing.

<Example of Configuration of Detection Apparatus 12>

Figure 3:
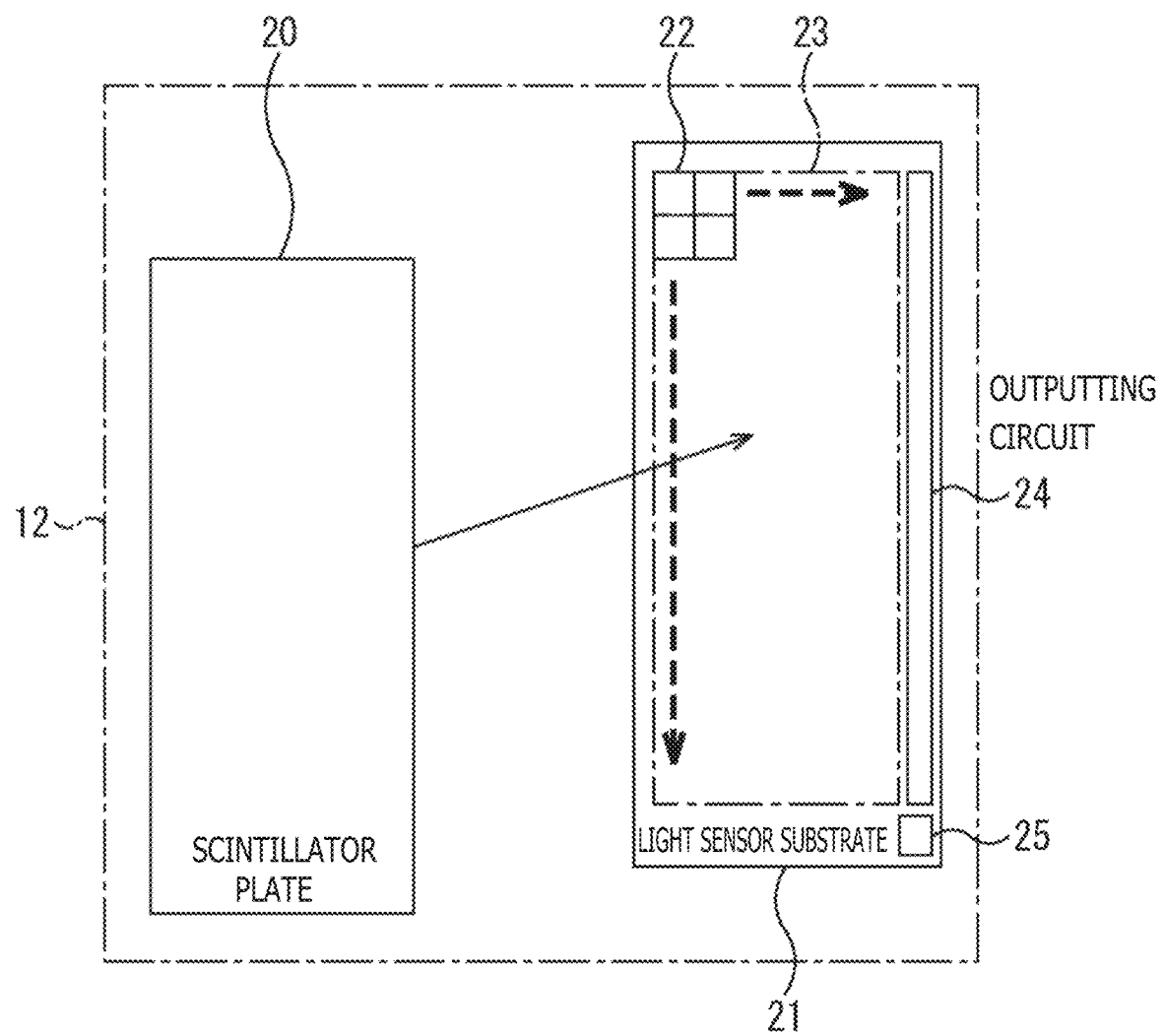
FIG. 3 is a plan view depicting an example of a configuration of a detection apparatus 12.

FIG. 3 is a plan view depicting an example of a configuration of the detection apparatus 12.

The detection apparatus 12 is configured by pasting a plate-shaped scintillator plate 20 to a light sensor substrate 21 including, for example, Si. In FIG. 3, the detection apparatus 12 before the scintillator plate 20 is pasted to the light sensor substrate 21 is depicted.

The scintillator plate 20 principally includes a thin film of a scintillator including, for example, columnar crystal CsI: Tl. An X-ray incident on a surface of the scintillator plate 20 is converted into scintillation light that is a visible ray.

A scintillator film thickness of the scintillator plate 20 is optimized depending upon the application such that the scintillation light is not dispersed in a planar form as far as possible. For example, in mammography use, the X-ray irradiation apparatus 11 applies an X-ray having comparatively low energy (approximately 15 to 45 keV) and, in this case, approximately 150 µm is adopted for the scintillator film thickness. Further, for example, in use for dental clinic or for imaging of internal organs such as a blood vessel or the heart, the X-ray irradiation apparatus 11 applies an X-ray having comparatively high energy (approximately 100 to 130 keV) and, in this case, approximately 600 µm is adopted as the scintillator film thickness.

The light sensor substrate 21 can be manufactured utilizing, for example, a manufacturing process of a semiconductor Si.

A light detection unit 23, an outputting circuit 24, and a timing controlling circuit 25 are formed on the light sensor substrate 21.

The light detection unit 23 is configured by arranging a plurality of light detection blocks 22 two-dimensionally in an array. Although the scintillator plate 20 is pasted to a face side of the light sensor substrate 21 on which the light detection unit 23 is formed, the light detection block 22 detects scintillation light at a portion of the scintillator plate 20 opposing to the light detection block 22 and outputs data obtained from an electric signal corresponding to the scintillation light.

In particular, the light detection block 22 performs light detection for detecting scintillation light after every predetermined unit period of time and A/D (Analog to Digital) converts an electric signal obtained by the light detection and corresponding to the scintillation light. Further, the light detection block 22 compresses the data amount of the electric signal after the A/D conversion and transmits data obtained as a result of the compression to the outputting circuit 24.

The outputting circuit 24 outputs the data outputted from the light detection block 22 of the light detection unit 23 to the outside of the detection apparatus 12.

The timing controlling circuit 25 controls the timing of operation of the light detection block 22 and the outputting circuit 24.

<Example of Configuration of Light Detection Block 22>

Figure 4:
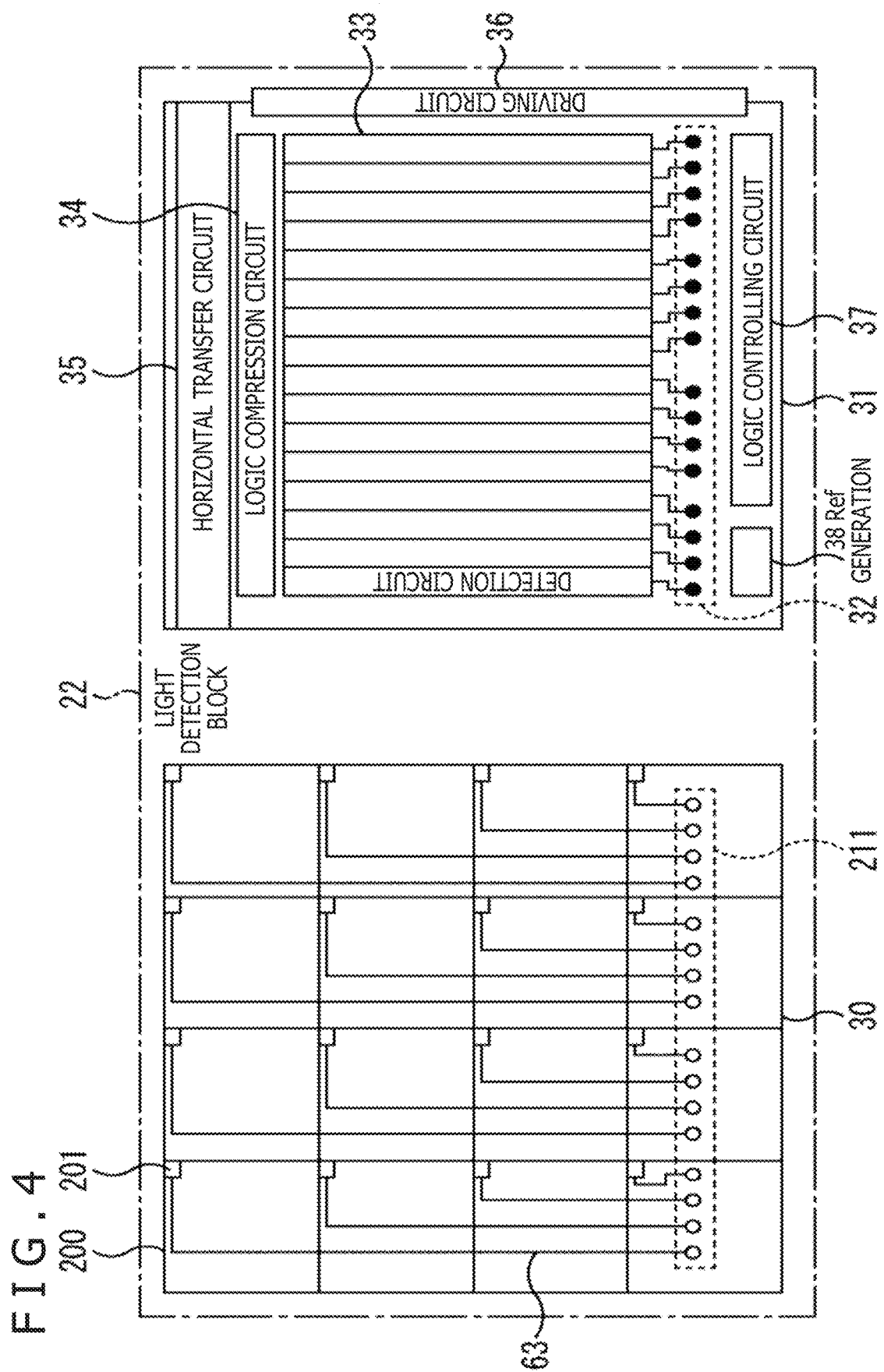
FIG. 4 is a plan view depicting an example of a configuration of a light detection block 22.

FIG. 4 is a plan view depicting an example of a configuration of the light detection block 22 of FIG. 3.

The light detection block 22 is configured such that at least a pixel substrate 30 and a detection circuit substrate 31 as two Si substrates are stacked.

Here, in FIG. 4, in order to avoid complicated depiction, the pixel substrate 30 and the detection circuit substrate 31 are not depicted in a stacked state and the pixel substrate 30 and the detection circuit substrate 31 are depicted in plan views.

A plurality of (active) pixels 200 and a connection unit 211 are formed on the pixel substrate 30.

On the pixel substrate 30, the plurality of pixels 200 is disposed two-dimensionally in an array. Although, in FIG. 4, the pixels 200 of 4×4 pixels in horizontal×vertical are arranged on the pixel substrate 30, the arrangement of the pixels 200 on the pixel substrate 30 is not limited to 4×4 pixels.

Each pixel 200 includes a pixel Tr (transistor) 201. Further, the pixel 200 includes a PD, an amplifier, and so forth not depicted in FIG. 4, and receives scintillation light incident on the pixel 200 and reads out and outputs a pixel signal corresponding to the scintillation light.

The pixel Tr 201 performs reading out of a pixel signal from the pixel 200 and supplies the pixel signal to the connection unit 211 through a vertical signal line 63.

The connection unit 211 is connected to a connection unit 32 of the detection circuit substrate 31 when the pixel substrate 30 and the detection circuit substrate 31 are in a stacked state. Consequently, the pixel substrate 30 and the detection circuit substrate 31 are electrically connected to each other such that an electric signal can be exchanged between the pixel substrate 30 and the detection circuit substrate 31.

For example, a pixel signal read out from a pixel 200 by the pixel Tr 201 is transmitted to (the connection unit 32 of) the detection circuit substrate 31 through the connection unit 211.

The detection circuit substrate 31 is stacked to a rear face side of a light receiving face of the pixel 200 of the pixel substrate 30.

On the detection circuit substrate 31, the connection unit 32, a plurality of detection circuits 33, a logic compression circuit 34, a horizontal transfer circuit 35, a driving circuit 36, a logic controlling circuit 37, and a reference signal generation (Ref generation) circuit 38 are formed.

The connection unit 32 is connected to the connection unit 211 of the pixel substrate 30 when the pixel substrate 30 and the detection circuit substrate 31 are in a stacked state. Further, the connection unit 32 is connected to the detection circuits 33 such that a pixel signal read out from the pixel 200 of the pixel substrate 30 is supplied to the detection circuit 33 through the vertical signal line 63 and the connection units 211 and 32.

The detection circuits 33 perform at least A/D conversion for a pixel signal supplied from the pixel 200 of the pixel substrate 30 through the vertical signal line 63 and the connection units 211 and 32 to detect an X-ray from which emission of scintillation light corresponding to the pixel signal is originated, and output an A/D conversion result (digital value) of the pixel signal as a detection result of the X-ray.

In FIG. 4, one detection circuit 33 is allocated to one pixel 200, and accordingly, on the detection circuit substrate 31, 16 detection circuits 33, the number of which is equal the number of the pixels 200 of 4×4 pixels, are provided.

In FIG. 4, the detection circuits 33 take charge of A/D conversion of pixel signals of the pixels 200 allocated to the detection circuits 33.

It is to be noted that it is possible to allocate one detection circuit 33 to a plurality of pixels 200 such as two pixels 200, i.e., to share one detection circuit 33 with a plurality of pixels 200. In this case, the number of detection circuits 33 to be provided on the detection circuit substrate 31 decreases. Further, in this case, the detection circuit 33 time-divisionally performs A/D conversion of pixel signals of a plurality of pixels 200 sharing the detection circuit 33.

In the A/D conversion performed by the detection circuit 33, the quantization width (quantization unit) can be adjusted.

Here, as an operation mode of the X-ray imaging apparatus (FIG. 1), an integration mode and a photon count mode are available.

In the integration mode, charge corresponding to scintillation light generated by the scintillator plate 20 in response to an X-ray is accumulated integrally into the pixel 200, and a pixel signal of a wide dynamic range corresponding to the integrally accumulated charge is outputted. The integration mode is an operation mode suitable for detection of an X-ray of a high dose in such a case that, for example, tomography is performed by cone beam CT or tomosynthesis, or the like.

In the photon count mode, charge corresponding to scintillation light generated by the scintillator plate 20 in response to an X-ray is accumulated into the pixel 200, and a pixel signal corresponding to the charge is outputted. However, as the pixel signal, for example, a pixel signal of a micro level corresponding to one photon of an X-ray is outputted. The photon count mode is an operation mode suitable for detection of an X-ray of a low dose in such a case that, for example, capturing of a two-dimensional projection image is performed, or the like.

In the integration mode, the dose of X-rays to be generated by the X-ray irradiation apparatus 11 (FIG. 1) is made a high dose, and in the photon count mode, the dose of X-rays to be generated by the X-ray irradiation apparatus 11 is made a low dose. Further, as occasion demands, in the integration mode, exposure time for the pixels 200 is set long, but in the photon count mode, the exposure time for the pixels 200 is set short.

In regard to A/D conversion of the detection circuits 33, in the integration mode, the quantization width is adjusted to a great quantization width corresponding to a pixel signal of one electron (or hole) or more, and a pixel signal of a wide dynamic range is converted into a digital value that can represent the wide dynamic range.

On the other hand, in the photon count mode, the quantization width is adjusted to a small quantization width corresponding to a pixel signal of less than one electron (or hole), and a pixel signal of a micro level is converted into a digital value of low quantization noise.

A digital value of a pixel signal (A/D conversion result) of each pixel 200 outputted from the detection circuits 33 is transmitted to the logic compression circuit 34.

The logic compression circuit 34 performs compression of digital values of pixel signals of the pixels 200 from the detection circuits 33 for reducing the digital values by various methods.

For example, in the case where the gradation of A/D conversion of the detection circuits 33 is represented by 10 bits, to the logic compression circuit 34, a digital value (binary data) configured from digital values of 10 bits of pixel signals of 16 pixels 200, i.e., a digital value of 16×10=160 bits, is supplied (transferred) from 16 detection circuits 33.

For example, the logic compression circuit 34 compresses digital values of 10 bits of the pixel signals of the 16 pixels 200 by adding the digital values of the pixel signals of the plurality of pixels 200. In particular, for example, taking neighboring pixels 200 of 2×2 pixels as one unit, the logic compression circuit 34 adds the digital values of 10 bits of the pixel signals of the pixels 200 of 2×2 pixels and outputs a sum value obtained as a result of the addition as a pixel value of one unit. In this case, the logic compression circuit 34 outputs pixel values of (a gradation of) 12 bits for only four (=16/(2×2)) units.

Accordingly, 16×10=160 bits that are a digital value of the pixel signals of the 16 pixels 200 are compressed into 12×4=48 bits that are a pixel value for four units.

Since the logic compression circuit 34 performs compression of digital values of pixel signals in such a manner as described above, it is possible to reduce the data amount of data for a projection image to be outputted from the detection apparatus 12 and to output data, for example, for a projection image of one frame, in a short period of time. Accordingly, it is possible to perform high speed imaging and obtain a projection image of a radiation in a short period of time.

A digital value outputted from the logic compression circuit 34 is supplied to the horizontal transfer circuit 35.

The horizontal transfer circuit 35 includes, for example, a shift register, stores a plurality of digital values (pixel values) outputted from the logic compression circuit 34 into the shift register, and successively transfers the plurality of digital values in the shift register until they are supplied to the outputting circuit 24 (FIG. 3).

A/D conversion of the detection circuits 33 and transfer of digital values of the horizontal transfer circuit 35 are executed in parallel in a pipeline manner, and while digital values in a certain unit period of time (frame) are horizontally transferred in the horizontal transfer circuit 35, the detection circuits 33 A/D convert pixel signals for a next unit period of time.

The driving circuit 36 drives the pixels 200 of the pixel substrate 30. In particular, the driving circuit 36 is connected to a drive line (not depicted) for each pixel 200 of the pixel substrate 30 through a connection unit not depicted but similar to the connection units 32 and 211. The driving circuit 36 supplies a driving signal to the drive line for each pixel 200 to drive all of the pixels 200 of the pixel substrate 30 in parallel at once, for example.

The logic controlling circuit 37 appropriately controls driving of internal circuitry of each block configuring the light detection block 22 under the control of the timing controlling circuit 25 (FIG. 3).

The reference signal generation circuit 38 generates a reference signal to be used for A/D conversion of the detection circuits 33 and supplies the reference signal to the detection circuits 33. The reference signal is, for example, a signal including a slope unit in which the level (voltage) decreases with a predetermined fixed inclination.

It is to be noted that, while, in FIG. 4, pixels 200 of 4×4 pixels are disposed on one pixel substrate 30, actually, a greater number of pixels 200, that is, for example, pixels 200 of 128×128 pixels are disposed on the pixel substrate 30. In this case, if it is assumed that the planar size of each pixel 200 is, for example, 50 μm square, then the planar size of the light detection block 22 is approximately 6.4 mm square.

<Photon Count Mode>

Figure 5:
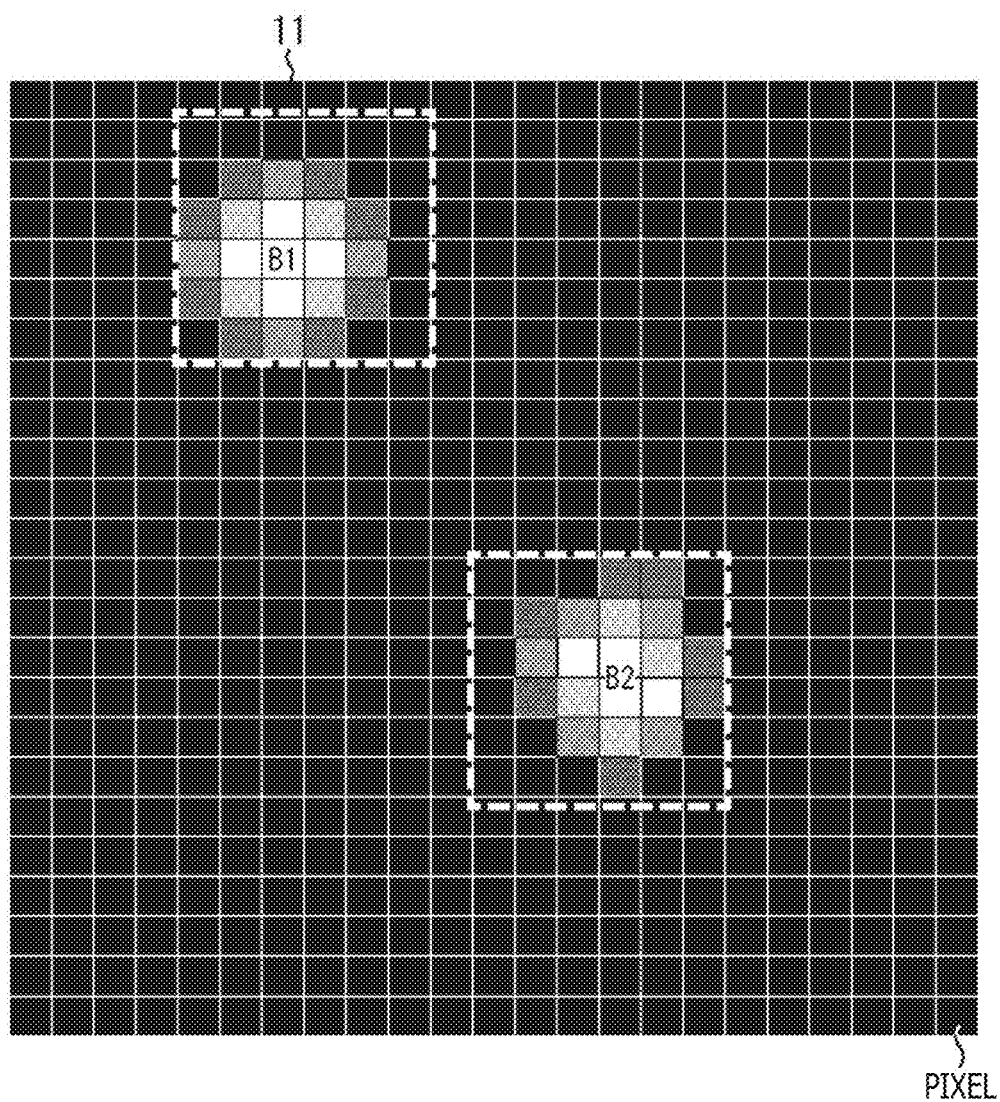
FIG. 5 is a plan view depicting an example of a pixel value of each pixel 200 obtained after A/D conversion of pixel signals of the pixels 200 of the light detection block 22 in a photon count mode.

FIG. 5 is a plan view depicting an example of pixel values of the pixels 200 (digital values of pixel signals) obtained after A/D conversion of pixel signals of the pixels 200 of the light detection block 22 in the photon count mode.

It is to be noted that, in FIG. 5, a darker portion represents that a pixel value is lower while a lighter portion represents that a pixel value is higher.

FIG. 5 depicts pixel values of 24×24 pixels (horizontal× vertical).

In the photon count mode, the X-ray irradiation apparatus (FIG. 1) irradiates the subject 1 with X-rays of a low dose, and the detection apparatus 12 receives, at the pixels 200 thereof, scintillation light corresponding to the X-rays transmitted through the subject 1 to perform capturing of a projection image corresponding to the X-rays.

In the photon count mode, the unit period of time for imaging, i.e., the exposure time for capturing of a projection image of one frame, is set to a short period of time such as, for example, approximately 10 μs. In this case, the frame rate is a very high rate of 100,000 fps (frame per second). It is to be noted that the frame rate is a rate limited by a period of time required for A/D conversion of the detection circuits 33 and a period of time required for transfer of a digital value of the horizontal transfer circuit 35.

In this manner, in the photon count mode, imaging in a short exposure time is performed using X-rays of a low dose.

Now, if the scintillator plate 20 having, for example, a scintillator layer of 150 μm thick is used for mammography, then one photon of an X-ray is incident on the scintillator plate 20, and approximately 200 photons of scintillation light are generated.

In FIG. 5, two photons of X-rays are incident on the detection apparatus 12, and (photons of scintillation light generated by) the two photons are individually observed as bright spots B1 and B2 having a diameter of approximately 300 μm.

In the photon count mode in which imaging in a short exposure time using X-rays of a low dose is performed, pixel signals outputted from almost all pixels 200 are dark pixel signals that include noise, and it is useless even if a digital value representative of a gradation of such dark pixel signals is outputted from the light detection block 22.

Therefore, for example, for digital values of pixel signals of the pixels 200 from the detection circuits 33, the logic compression circuit 34 performs a threshold value process using a threshold value that is a predetermined low value and deems any digital value equal to or lower than the threshold value as fully dark (zero) to thereby compress the gradations for the digital value, and the data amount of digital values to be outputted from the logic compression circuit 34 can be reduced.

In this case, by using the digital values, that are outputted from the logic compression circuit 34 and whose gradations have been compressed, as data of bright spots arising from photons of X-rays and processing the data of the bright spots, an X-ray projection image can be generated.

Further, the logic compression circuit 34 determines, for example, a region of a predetermined size such as 6×6 pixels as indicated by a broken line in FIG. 5 as a detection region for detecting a peak (maximum value) of a pixel value (digital value), and scans the detection region with a pitch of the pixels 200. Then, the logic compression circuit 34 detects a peak of the sum total of digital values of the pixel signals of the pixels 200 in the detection region and can thereby output the position of the detection region at which the peak of the predetermined value or more is obtained and the peak, as data of a bright spot arising from a photon of the X-ray.

Where the logic compression circuit 34 outputs only a position of a detection region at which a peak of the predetermined value or more is obtained and the peak, as data of a bright spot arising from a photon of an X-ray in this manner as described above, the data amount to be outputted by the logic compression circuit 34 can be compressed (reduced) significantly.

As the position of a detection region (at which a peak of the sum total of digital values is obtained) as data of a bright spot, for example, a position of a center of the detection region (position at which two diagonals of a rectangular detection region of 6×6 pixels cross each other) or a position of a center of gravity at which the digital values of the pixel signals are regarded as weights can be adopted.

If the coordinates of the position of the center of gravity (at which the digital values of the pixel signals are regarded as weights) are represented by (Xc, Yc), the coordinates of each pixel 200 in the detection region are represented by (x, y), and the digital value of the pixel signal of the pixel 200 at the position (x, y) is represented by W(x, y), then the gravity center position (Xc, Yc) can be determined in accordance with the following expressions.

$$Xc=\Sigma(x \times W(x,y))/\Sigma W(x,y)$$

$$Yc=\Sigma(y \times W(x,y))/\Sigma W(x,y)$$

Here, in the expression (1), $\Sigma$ represents summation for all positions (x, y) of the pixels 200 in the detection region.

Reduction of the data amount to be outputted from the logic compression circuit 34 is effective especially in the case where imaging is performed at a high frame rate in the photon count mode.

It is to be noted that, for example, in the case where processing for compression of digital values of pixel signals by the logic compression circuit 34 is complicated and requires much time, the three processes of A/D conversion of the detection circuits 33, compression by the logic compression circuit 343, and transfer by the horizontal transfer circuit 35 can be pipelined such that they can be performed in parallel.

In the case where the logic compression circuit 34 outputs only a position of a detection region at which a peak of the sum total of digital values is obtained and the peak, as data of a bright point arising from a photon of an X-ray, an X-ray projection image can be generated deeming the position of the detection region at which the peak is obtained and the peak as the incident position on which a photon of an X-ray is incident and (a value corresponding to) the energy of the photon.

In this case, although the X-ray is optically diffused by the scintillator plate 20, the incident position of the X-ray can be determined either with a resolution of the pitch of the pixels 200 or with a finer resolution than the resolution of the pitch of the pixels 200.

Further, in this case, since the energy of the photon of the X-ray can also be specified together with the incident position of the X-ray, it is possible to utilize the energy to perform removal of a bright spot caused by diffused light of the X-ray (X-ray that has not transmitted the subject 1 straightforwardly), correction of the absorption rate of the X-ray for each energy level, discrimination of a substance configuring the subject 1, and so forth.

<Example of Configuration of Pixel 200>

Figure 6:
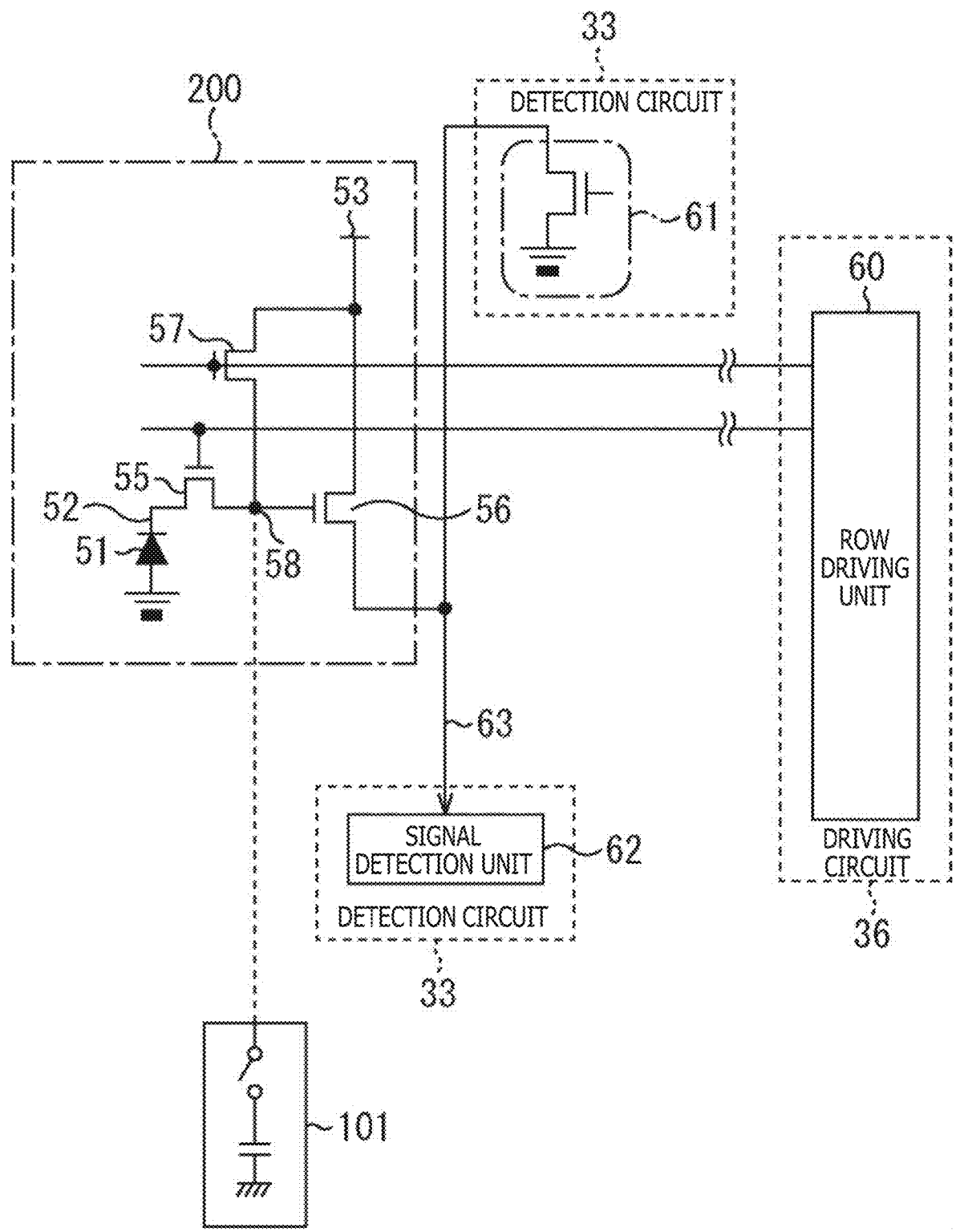
FIG. 6 is a circuit diagram depicting an example of a configuration of the pixel 200.

FIG. 6 is a circuit diagram of an equivalent circuit depicting an example of a configuration of the pixel 200 of FIG. 4.

Referring to FIG. 6, the pixel 200 includes a PD 51, a transfer Tr (transistor) 55, an amplification Tr 56, a reset Tr 57, and a detection node 58.

For the transfer Tr 55 to reset Tr 57, for example, an n-type MOSFET (Metal-Oxide Semiconductor Field Effect Transistor) is used.

The PD 51 has a planar shape of, for example, a substantially square shape. The PD 51 converts photons incident on the PD 51 into charge and accumulates the charge into an accumulation node 52 that is the cathode of the PD 51. In particular, the PD 51 generates a pair of an electron and a hole in response to incidence of a photon of scintillation light generated by the scintillator plate 20 and accumulates the electron into the accumulation node 52.

The PD 51 is an embedded type PD whose accumulation node 52 is depleted fully upon discharging of charge by resetting of the PD 51. In particular, if the accumulation node 52 is connected to a power supply line 53 through the transfer Tr 55, detection node 58, and reset Tr 57 to cause resetting by which electrons as charge accumulated in the accumulation node 52 are discharged to the power supply line 53, then all electrons or holes as the carrier are discharged from the PD 51 and potential is fixed only by fixed charge by the donor or the acceptor. At this time, even if a node having potential deeper than the abovementioned potential is connected to the accumulation node 52, the potential of the accumulation node 52 does not change.

The transfer Tr 55 transfers charge accumulated in the accumulation node 52 to the detection node 58 under the control of a row driving unit 60 configuring the driving circuit 36 of the light detection block 22 in FIG. 4.

The amplification Tr 56 is connected at the gate thereof to the detection node 58, at the drain thereof to the power supply line 53, and at the source thereof to a vertical signal line 63, and drives the vertical signal line 63 having a high load in response to a voltage of the detection node 58 applied to the gate.

The amplification Tr 56 forms a source follower together with a constant current source 61 that configures the detection circuits 33 of FIG. 4 and transmits a voltage of the detection node 58 to the vertical signal line 63 with a gain lower than 1. The voltage transmitted to the vertical signal line 63 is outputted as a pixel signal read out from the pixel 200 to a signal detection unit 62 that configures the detection circuit 33.

The reset Tr 57 is connected at the gate thereof to the row driving unit 60, at the drain thereof to the power supply line 53, and at the source thereof to the detection node 58, and performs resetting of the detection node 58 by discharging charge accumulated in the detection node 58 to the power supply line 53. Further, the reset Tr 57 performs resetting of (the accumulation node 52 of) the PD 51 by discharging charge accumulated in the accumulation node 52 to the power supply line 53 through the transfer Tr 55.

The detection node 58 is an FD (Floating Diffusion), and accumulates charge transferred thereto from the PD 51 through the transfer Tr 55 and generates a voltage of an analog value according to the accumulated charge amount. The voltage is applied to the gate of the amplification Tr 56.

In FIG. 6, the row driving unit 60 configures the driving circuit 36 (FIG. 4) and drives the transfer Tr 55 and the reset Tr 57.

In particular, the row driving unit 60 controls, for example, the transfer Tr 55 and the reset Tr 57 to an on state at the same time to allow electrons as charge accumulated in the accumulation node 52 to be discharged to the power supply line 53 through the transfer Tr 55 and the reset Tr 57 and to allow electrons as charge accumulated in the detection node 58 to be discharged to the power supply line 53 through the reset Tr 57. Consequently, the pixel 200 is reset (initialized) to a dark state before the PD 51 accumulates charge, i.e., to a state in which photons of scintillation light are not incident as yet.

Further, the row driving unit 60 controls only the transfer Tr 55 to an on state to allow charge accumulated in (the accumulation node 52 of) the PD 51 to be transferred to the detection node 58 through the transfer Tr 55.

Furthermore, the row driving unit 60 controls only the reset Tr 57 to an on state to allow charge accumulated in the detection node 58 to be discharged to the power supply line 53 through the reset Tr 57 to initialize the charge amount of the detection node 58 (reset the detection node 58).

In FIG. 6, the constant current source 61 and the signal detection unit 62 configure the detection circuit 33. The constant current source 61 includes, for example, a MOSFET or the like and supplies fixed current to the vertical signal line 63. The signal detection unit 62 performs A/D conversion and so forth for a pixel signal read out from the pixel 200 into the vertical signal line 63.

Here, the transfer Tr 55, amplification Tr 56, and reset Tr 57 are the pixel Trs 201 (FIG. 4).

In the pixel 200, the PD 51 photoelectrically converts scintillation light incident on the PD 51 and accumulates charge obtained by the photoelectric conversion for a predetermined exposure time after it is reset. Then, in the pixel 200, after lapse of the exposure time, the transfer Tr 55 is temporarily turned on to allow the charge accumulated in the PD 51 to be transferred to the transfer Tr 55, and a pixel signal corresponding to the charge is read out into the vertical signal line 63.

In the pixel 200, accumulation of charge during the exposure time into the PD 51 and reading out of a pixel signal corresponding to the charge are performed repeatedly, and consequently, a pixel signal corresponding to the light amount of photons of scintillation light incident on the PD 51 during the exposure time is acquired.

Incidentally, the characteristic of the PD 51 of the embedded type adopted in the pixel 200 is that the accumulation node 52, which is the cathode of the PD 51, and the detection node 58 are not capacitively coupled to each other upon reading out. As a result, the conversion efficiency in photoelectric conversion of the PD 51 increases and the sensitivity to incidence of one photon can be improved as the parasitic capacitance of the detection node 58 is reduced. Further, even if the size of the PD 51 is increased, the conversion efficiency does not deteriorate, and therefore, as the PD 51 is increased in size, the sensitivity per one pixel of the pixel 200 to incidence of light of a same luminous flux density can be improved.

Further, since the pixel 200 does not accompany electron doubling that increases electrons as charge, a pixel signal read out from the pixel 200 is influenced by noise (read out noise) arising from the amplification Tr 56 or a circuit that is included in the detection circuit 33 at the succeeding stage and performs A/D conversion.

However, if the sensitivity of the pixel 200 is improved, then the influence of read out noise on a pixel signal can be reduced relatively as described hereinabove. For example, by reducing the parasitic capacitance of the detection node 58 as far as possible and increasing the PD 51 in size as far as possible within a range within which one electron can move inside the PD 51 by drift, the S/N (Signal to Noise ratio) of the pixel signal to be read out from the pixel 200 can be maximized to thereby implement the light detection block 22 as an ultra-high sensitivity detector that detects an X-ray with ultra-high sensitivity.

The structure of the pixel 200 that adopts the PD 51 of the embedded type having the accumulation node 52 that is to be fully depleted is much different from the structure of a PD that has been used for existing imaging of transmission light of an X-ray. The pixel 200 reacts, with high degree accuracy, with incidence of few photons and can quickly output a pixel signal to the signal detection unit 62 through the vertical signal line 63.

It is to be noted that, although the structure of the pixel 200 is similar to the structure of a pixel of a CMOS (Complementary Metal Oxide Semiconductor) image sensor that is used in a digital camera and so forth, the design concept is quite different.

As the area of the pixel 200 increases, it becomes easier to increase the area of the PD 51 to increase the aperture ratio, and to reduce the number of pixels 200 to be shared by the detection circuit 33 to easily achieve speeding up. In particular, although one detection circuit 33 can be shared by a plurality of pixels 200 as described hereinabove with reference to FIG. 4, in the case where the area of the PD 51 and therefore of the pixel 200 is increased, since the area that can be occupied by the detection circuit 33 can have room, the number of pixels 200 by which one detection circuit 33 is shared can be decreased. For example, in the case where the planar size of the pixel 200 is 50 μm square, one detection circuit 33 can be allocated to one pixel 200 as described hereinabove with reference to FIG. 4. Furthermore, in this case, it is possible to implement such a high frame rate of, for example, 100,000 fps, or the like.

Further, in the case where the area of (the PD 51 of) the pixel 200 is increased, floor noise in a diffusion area of scintillation light corresponding to one photon of an X-ray decreases.

Therefore, preferably, the area of the pixel 200 is made, for example, equal to or greater than 400 μm².

Upon increase in size of the pixel 200, the upper limit to the area of the pixel 200 is defined (restricted) by the movement of electrons in the PD 51 of the embedded type by drift. In regard to the pixel 200, it is necessary to design the potential in the PD 51 such that one electron generated at a remote end in the PD 51 is transferred at a high speed to the detection node 58.

It is to be noted that, although it is presupposed herein that the n-type diffusion layer that is the cathode of the PD 51 serves as the accumulation node 52 into which electrons are accumulated, all of the polarities may be reversed such that a p-type diffusion layer that is the anode of the PD 51 serves as the accumulation node 52 into which holes are accumulated.

<Operation of Pixel 200 and Signal Detection Unit 62>

Figure 7:
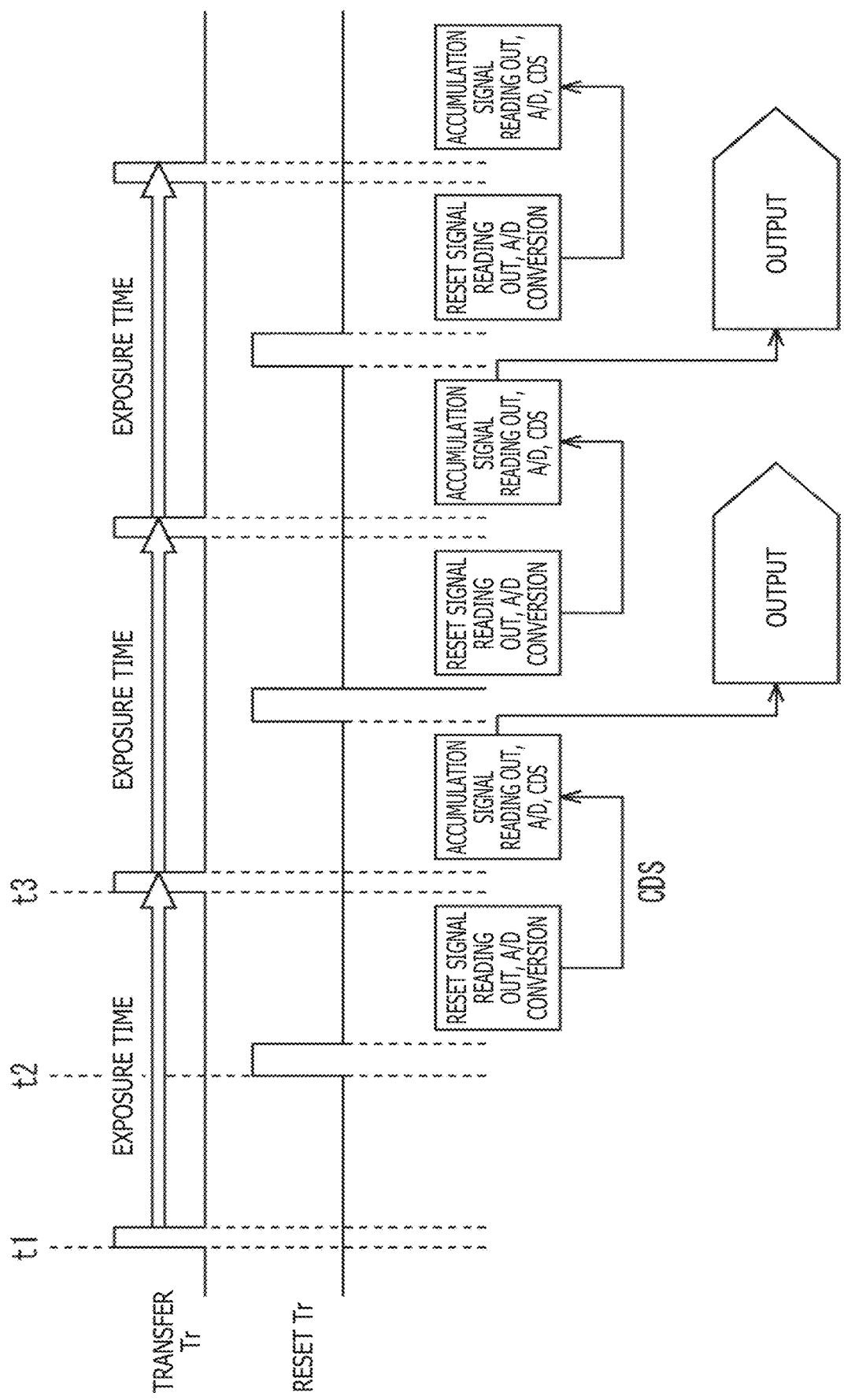
FIG. 7 is a timing chart illustrating an example of operation of the pixel 200 and a signal detection unit 26 (FIG. 6) of a detection circuit 33.

FIG. 7 is a timing chart illustrating an example of operation of the pixel 200 and the signal detection unit 26 of the detection circuit 33 (FIG. 6).

In the present embodiment, since one detection circuit 33 is allocated to one pixel 200 in the light detection block 22, in each light detection block 22, all pixels 200 operate at once.

It is to be noted that, in the case where one detection circuit 33 is allocated, for example, to two pixels 200 and the one detection circuit 33 and the two pixels 200 are connected to each other through the vertical signal line 63, a pass transistor for selecting a pixel 200 to be connected to the detection circuit 33 is provided between the pixel 200 and the vertical signal line 63. Further, the two pixels 200 are selected alternatively and connected to the one detection circuit 33, and the detection circuit 33 performs A/D conversion of a pixel signal outputted from the pixel 200 connected to the detection circuit 33, among the two pixels 200, in the following manner.

The signal detection unit 62 of the detection circuit 33 performs A/D conversion of a reset signal as a pixel signal corresponding to charge accumulated in the detection node 58 (FIG. 6) in a dark state in which photons of scintillation light are not incident on the PD 51 and A/D conversion of an accumulation signal as a pixel signal corresponding to charge accumulated in the PD 51 during the exposure time and transferred to the detection node 58.

Further, the signal detection unit 62 performs CDS (Correlated Double Sampling) of cancelling various kinds of noise by subtracting an A/D conversion result of the reset signal from an A/D conversion result of the accumulation signal, and outputs the reset signal or the accumulation signal as a read out pixel value (digital value) of the pixel 200.

In FIG. 7, at time t1, the row driving unit 60 temporarily turns on the transfer Tr 55. When the transfer Tr 55 is turned on, charge accumulated in the accumulation node 52 of the PD 51 is transferred to the detection node 58.

Thereafter, if the transfer Tr 55 is turned off, then the accumulation node 52 is placed into a floating state and starts accumulation of new charge generated by incidence of light on the PD 51.

At time t2 after the transfer Tr 55 is turned off, the row driving unit 60 temporarily turns on the reset Tr 57. When the reset Tr 57 is turned on, charge accumulated in the detection node 58 is discharged to the power supply line 53.

Thereafter, when the reset Tr 57 is turned off, the potential of the detection node 58 drops a little from a reference potential through coupling to the gate of the reset Tr 57 and enters a floating state. In the FD that is the detection node 58, charge that becomes significant noise called kTC noise arising from the capacitance of the FD is generated.

In the pixel 200, immediately after the reset Tr 57 is turned off, a pixel signal corresponding to the charge accumulated in the detection node 58 is read out as a reset signal (first time reading out of a signal to be used for the CDS) and is supplied to the signal detection unit 62 through the vertical signal line 63.

The signal detection unit 62 performs A/D conversion of the reset signal supplied from the pixel 200 in such a manner as described above.

Thereafter, at time t3, the row driving unit 60 temporarily turns on the transfer Tr 55 similarly as in the case as at time t1. When the transfer Tr 55 is turned on, charge accumulated in the accumulation node 52 of the PD 51 is transferred to the detection node 58. At this time, if the potential of the detection node 58 is sufficiently deep, then electrons as charge accumulated in the accumulation node 52 are all transferred to the detection node 58, and the accumulation node 52 is placed into a fully depleted state.

Thereafter, when the transfer Tr 55 is turned off, the accumulation node 52 is placed into a floating state and starts accumulation of new charge generated by incidence of light on the PD 51.

Further, during an exposure time that is a period starting after the transfer Tr 55 is turned off at time t1 and ending when the transfer Tr 55 is turned off at time t3, charge accumulated in the accumulation node 52 is transferred to the detection node 58, and a voltage corresponding to the charge is maintained in the detection node 58.

In particular, at time t3 while the transfer Tr 55 remains to be turned on, charge accumulated in the accumulation node 52 during the exposure time is transferred from the accumulation node 52 to the detection node 58 through the transfer Tr 55. Consequently, the potential of the detection node 58 drops by an amount corresponding to the charge transferred from the accumulation node 52 in comparison with that before the charge is transferred from the accumulation node 52 to the detection node 58, and the potential of the detection node 58 becomes shallower.

In the pixel 200, a pixel signal corresponding to the charge accumulated in the detection node 58 after the transfer Tr 55 is turned off at time t3 is read out as an accumulation signal (second time reading out of a signal to be used for the CDS) and is supplied to the signal detection unit 62 through the vertical signal line 63.

The signal detection unit 62 performs A/D conversion of an accumulation signal supplied from the pixel 200, in such a manner as described above.

After A/D conversion of the accumulation signal is performed, the signal detection unit 62 subtracts the immediately preceding A/D conversion result of the reset signal from the A/D conversion result of the accumulation signal to perform CDS. By such CDS, it is possible to delete (cancel) low frequency noise generated in the pixel 200 and including kTC noise and noise that mixes into the accumulation signal (and the reset signal) in the A/D conversion to thereby obtain a digital value of the pixel signal corresponding to the charge generated by light incident on the PD 51 during the exposure time.

Accumulation of charge into the PD 51 during an exposure time, reading out of a reset signal and an accumulation signal from the pixel 200, and A/D conversion of the reset signal and the accumulation signal read out from the pixel 200 (and CDS using the reset signal and the accumulation signal after the A/D conversion) are performed repeatedly.

It is to be noted that A/D conversion (and CDS) of a reset signal and an accumulation signal, transfer of a digital value obtained by the A/D conversion from the detection circuit substrate 31 (FIG. 4) to the outputting circuit 24 (FIG. 3), and outputting of the digital value from the outputting circuit 24 to the outside are pipelined and performed in parallel.

<Example of Configuration of Detection Circuit 33>

Figure 8:
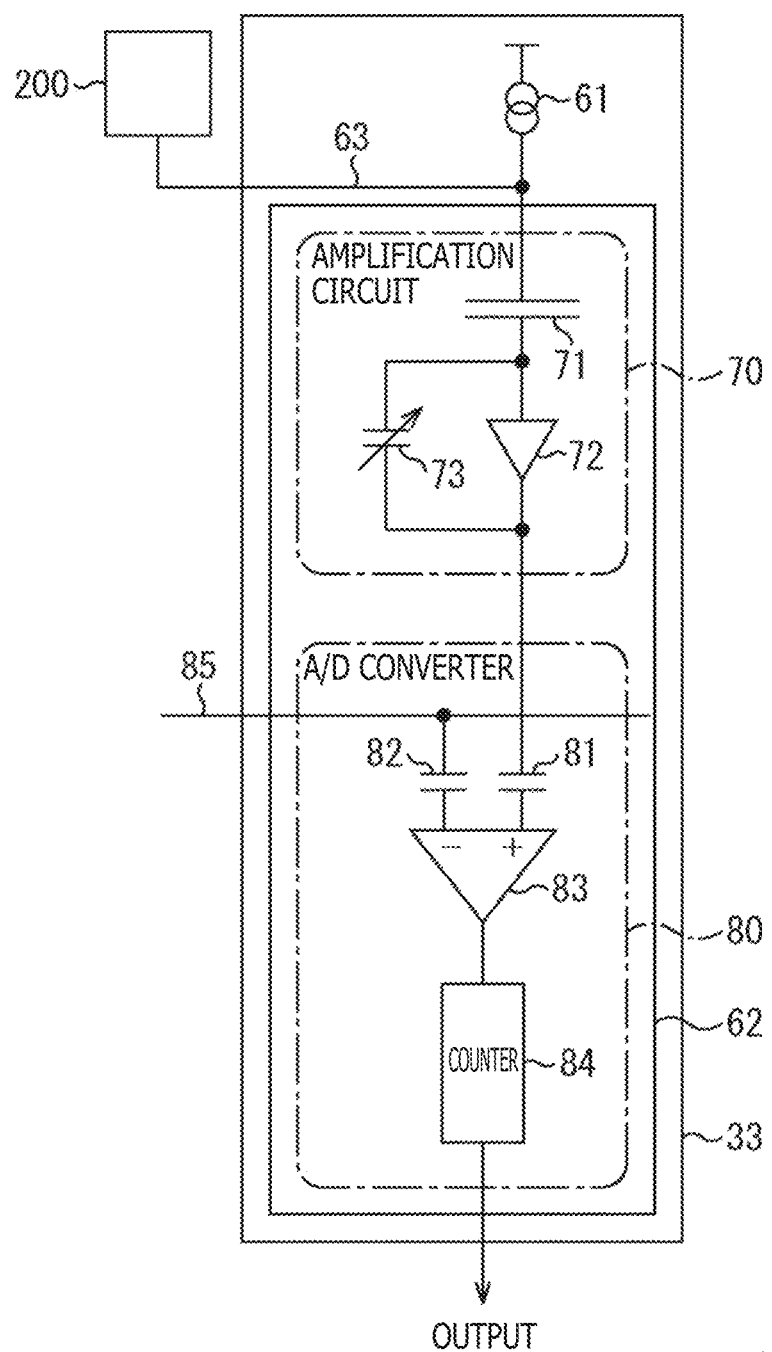
FIG. 8 is a view depicting an example of a configuration of the detection circuit 33.

FIG. 8 is a view depicting an example of a configuration of the detection circuit 33 of FIG. 4.

The detection circuit 33 includes the constant current source 61, an amplification circuit 70, and an A/D converter 80. The amplification circuit 70 and the A/D converter 80 configure the signal detection unit 62.

The constant current source 61 is connected to the vertical signal line 63 and configures a source follower together with the amplification Tr 56 connected to the vertical signal line 63 and configuring the pixel 200.

The amplification circuit 70 includes a capacitor 71, an amplifier (operational amplifier) 72, and a variable capacitor 73.

The capacitor 71 is connected at one end thereof to the vertical signal line 63 and at the other end thereof to an input terminal of the amplifier 72. Accordingly, a pixel signal (reset signal, accumulation signal) read out from the pixel 200 is inputted to the amplifier 72 through the capacitor 71.

The input terminal of the amplifier 72 is connected not only to the capacitor 71 but also to one end of the variable capacitor 73, and the output terminal of the amplifier 72 is connected to the other end of the variable capacitor 73.

The amplification circuit 70 amplifies a pixel signal read out from the pixel 200 into the vertical signal line 63 with a predetermined gain and outputs the resulting pixel signal to the A/D converter 80.

The A/D converter 80 is an A/D converter of what is generally called a single slope type and includes capacitors 81 and 82, a comparator 83 and a counter 84.

The capacitors 81 and 82 are capacitors of the same capacitance for coupling, and one end of the capacitor 81 is connected to the non-inverting input terminal (+) of the comparator 83 and one end of the capacitor 82 is connected to the inverting input terminal (−) of the comparator 83.

To the other end of the capacitor 81, a pixel signal outputted from the amplification circuit 70 is supplied. Accordingly, the pixel signal outputted from the amplification circuit 70 is supplied to the non-inverting input terminal (+) of the comparator 83 through the capacitor 81.

The other end of the capacitor 82 is connected to a reference signal line 85. To the reference signal line 85, a reference signal outputted from the reference signal generation circuit 38 (FIG. 4) is supplied. Accordingly, the reference signal outputted from the reference signal generation circuit 38 is supplied to the inverting input terminal (−) of the comparator through the capacitor 82.

The comparator 83 compares a voltage as a pixel signal supplied to the non-inverting input terminal (+) thereof and a voltage as a reference signal supplied to the inverting input terminal (−) thereof with each other and supplies a result of the comparison to the counter 84.

The counter 84 counts a period of time starting after the reference signal begins to decrease with a fixed inclination and ending when the magnitude relationship between the reference signal and the pixel signal is inverted, in response to a result of comparison between (a voltage as) the pixel signal and (a voltage as) the reference signal from the comparator 83, and outputs a count value representative of the period of time as an A/D conversion result of the pixel signal. In particular, the counter 84 starts counting at a timing at which the reference signal begins to decrease with a fixed inclination and stops the counting when the magnitude relationship between the reference signal and the pixel signal inverts. The counter 84 outputs the count value when the counting has stopped, as an A/D conversion result of the pixel signal.

It is to be noted that the A/D converter 80 can perform, after it performs A/D conversion of a reset signal, A/D conversion of an accumulation signal and CDS simultaneously by performing, using an A/D conversion result of the reset signal as an initial value, counting of the count value as A/D conversion of the accumulation signal in a direction reverse to that in the case of the A/D conversion of the reset signal.

Here, counting of the count value as A/D conversion of the accumulation signal in a direction reverse to that in the case of the A/D conversion of the reset signal signifies that, for example, in the case where counting of decrementing the count value is performed in A/D conversion of a reset signal, counting of incrementing the count value is performed as A/D conversion of the accumulation signal.

The detection apparatus 12 includes an adjustment mechanism that variably adjusts the quantization width of A/D conversion of the A/D converter 80. The adjustment mechanism adjusts, for example, the quantization width of A/D conversion to a quantization width corresponding to a pixel signal lower than one electron or a quantization width corresponding to a pixel signal equal to or higher than one electron.

Here, in the photon count mode, the X-ray irradiation apparatus 11 outputs X-rays of a low dose, and from the scintillator plate 20 (FIG. 3) of the detection apparatus 12, scintillation light of, for example, several hundreds of photons is generated with respect to one photon of the X-rays and such scintillation light is diffused and incident on a plurality of pixels 200. Therefore, even at a pixel 200 on which scintillation light is incident, the number of photons of scintillation light incident on the pixel 200 is at a level of several photons, and the number of electrons as charge generated by incidence of the scintillation light is several electrons.

In the photon count mode, in order to detect a pixel signal of such several electrons (pixel signal corresponding to several electrons) with high accuracy, the quantization width of A/D conversion is adjusted to a quantization width corresponding to a pixel signal of less than one electron.

In particular, in the photon count mode, in order to reduce quantization noise, the quantization width of A/D conversion is adjusted to a small quantization width corresponding to a pixel signal that is, for example, sufficiently smaller than a pixel signal of one electron. Then, A/D conversion of a pixel signal read out from the pixel 200 is performed with the small quantization width.

On the other hand, in the integration mode, since the X-ray irradiation apparatus 11 outputs X-rays of a high dose, scintillation light generated by a plurality of photons of the X-ray is incident on the pixel 200, and the number of electrons as charge generated by incidence of the scintillation light sometimes becomes a maximum of several thousands.

Where the A/D converter 80 performs A/D conversion of, for example, 10 bits, since it is necessary to represent a pixel signal of (0 to) several thousands of electrons with $1024=2^{10}$ gradations, in order to appropriately represent a pixel signal of up to several thousands of electrons in a digital value, the quantization width of A/D conversion is adjusted to a large quantization width that corresponds to a pixel signal of one or more electrons, for example, of four electrons. Then, A/D conversion of a pixel signal read out from the pixel 200 is performed with the large quantization width.

As the adjustment mechanism for variably adjusting the quantization width of A/D conversion of the A/D converter 80 (hereinafter also referred to as quantization width adjustment mechanism), for example, the amplification circuit 70 can be adopted.

It is now assumed that the quantization width of A/D conversion of the A/D converter 80 in the case where the amplification circuit 70 does not exist and the inclination of the reference signal is a predetermined inclination (hereinafter also referred to as default quantization width) is a quantization width corresponding, for example, to a pixel signal of four electrons (hereinafter also referred to as quantization width for four electrons).

In this case, if the gain of the amplification circuit 70 is adjusted, for example, to 0 dB (one time), then the quantization width of A/D conversion of a pixel signal supplied to the A/D converter 80 through the amplification circuit 70 is adjusted substantially to a quantization width for four electrons that is the default quantization width.

On the other hand, if the gain of the amplification circuit 70 is adjusted, for example, to 24 dB (16 times), then the quantization width of A/D conversion of a pixel signal supplied to the A/D converter 80 through the amplification circuit 70 is adjusted substantially to a quantization width for 0.25 electrons that is $\frac{1}{16}$ the quantization width for four electrodes, which is the default quantization width. In this case, both quantization noise generated by quantization of A/D conversion and circuit noise of the A/D converter 80 decrease to $\frac{1}{16}$ in comparison with those in the case where the default quantization width is used.

As the quantization width adjustment mechanism, a mechanism other than the amplification circuit 70 can be adopted.

In particular, as the quantization width adjustment mechanism, for example, the reference signal generation circuit 38 can be adopted.

If the reference signal generation circuit 38 adjusts the inclination of decrease of the reference signal to $\frac{1}{16}$ that of the case of the default, a gain of 24 dB is applied to the A/D converter 80, and the quantization width can be adjusted substantially to $\frac{1}{16}$ that of the case of the default.

Further, it is possible, for example, to incorporate an amplifier of a variable gain for amplifying a pixel signal into the inside of the pixel 200 and to adopt the variable gain amplifier as the quantization width adjustment mechanism.

Furthermore, it is possible to connect, to the detection node 58 that is an FD of the pixel 200, the circuit 101 that includes a switch and a capacitor connected in series as depicted in FIG. 6, and to adopt the circuit 101 as the quantization width adjustment mechanism. The circuit 101 functions as a gain adjustment unit that adjusts the gain of a pixel signal to be supplied from the pixel 200 to the comparator 83 by turning on/off the switch. According to the circuit 101, it is possible to connect, by turning on the switch, the capacitor to the detection node 58 such that the pixel 200 has a negative gain to thereby adjust the quantization width substantially to a value higher than that where the switch of the circuit 101 is turned off.

In this manner, the detection apparatus 12 can include a quantization width adjustment mechanism that adjusts the quantization width of A/D conversion of the A/D converter 80, and by causing the quantization width adjustment mechanism to adjust the quantization width of A/D conversion to a quantization width corresponding to a pixel signal of less than one electron or to a quantization width corresponding to a pixel signal of one or more electrons, both an X-ray of a high dose and an X-ray of a low dose can be detected. In other words, even if a detection circuit for performing detection of an X-ray is not provided for each pixel 200, detection of an X-ray can be performed by the same detection circuit 33 in each of the photon count mode and the integration mode.

More particularly, without using a special material such as CdTe, it is possible to acquire an X-ray projection image by the photon counting method utilizing scintillation light and implement a wide dynamic range capable of withstanding high doses ready for tomography with the detection apparatus 12 that can detect an X-ray by the photon counting method.

Further, according to the detection apparatus 12, by reconstructing the pixel technology, circuit technology, and stacking technology having been established with a CMOS image sensor in recent years, high sensitivity and a high speed response required for the photon counting method can be achieved utilizing scintillation light and an FPD apparatus of the photon counting type can be implemented.

Furthermore, according to the detection apparatus 12, by increasing the sensitivity of the pixel 200, it is possible to significantly decrease the dose of an X-ray to be applied upon a subject 1 without degrading the picture quality of an X-ray projection image or to improve, if the dose of an X-ray is not reduced, the picture quality of an X-ray projection image significantly.

Further, by the detection apparatus 12 that counts X-rays of different energy bands independently of each other, it is possible to discriminate a substance utilizing transmittances of the X-rays that are different depending upon the substance.

Such a detection apparatus 12 as described above can be applied to an FPD apparatus for detecting an X-ray and so forth, which are utilized, for example, in the medical or security field.

<Different Examples of Pixel Capable of being Adopted in Pixel Substrate 30>

Figure 9A:
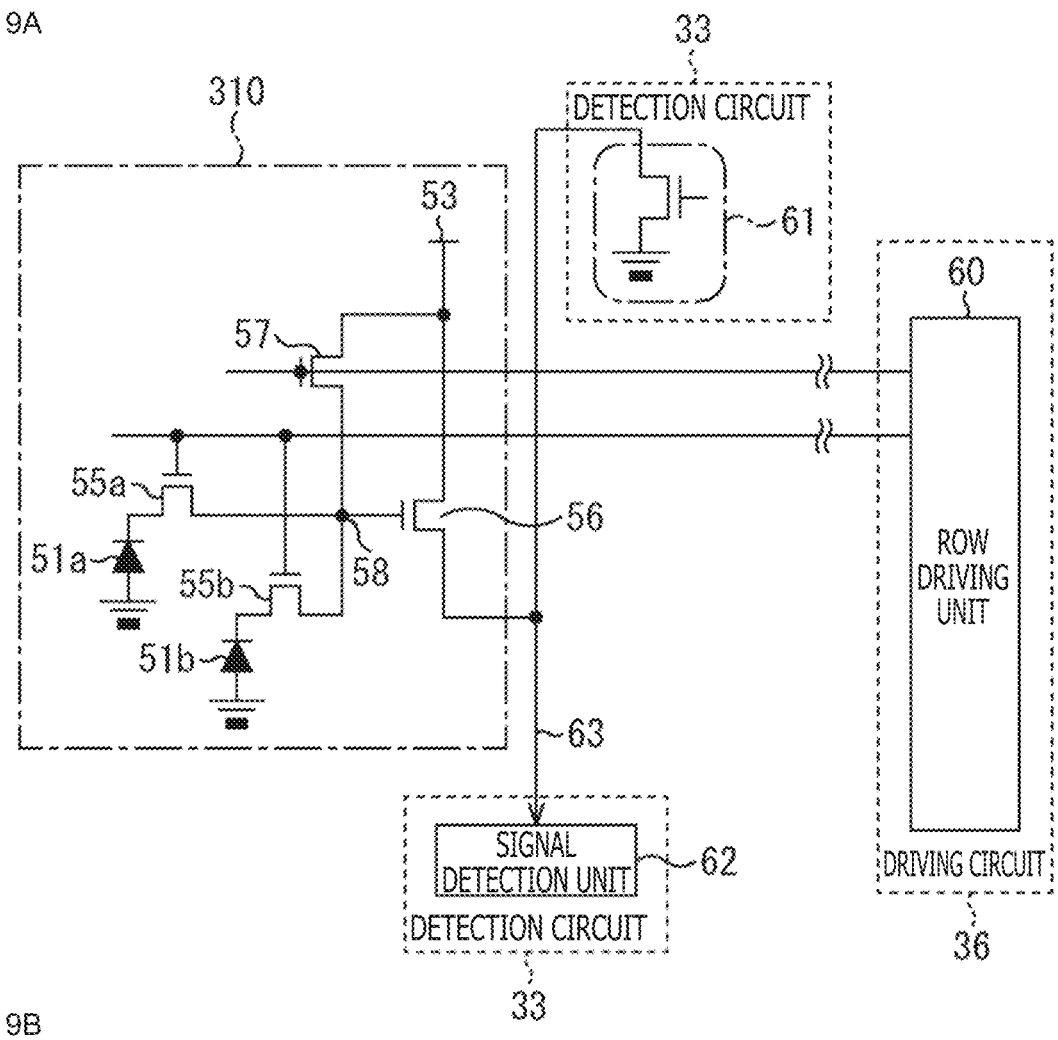
FIGS. 9A and 9B are views depicting a first different example of a pixel capable of being adopted in a pixel substrate 30.
Figure 9B:
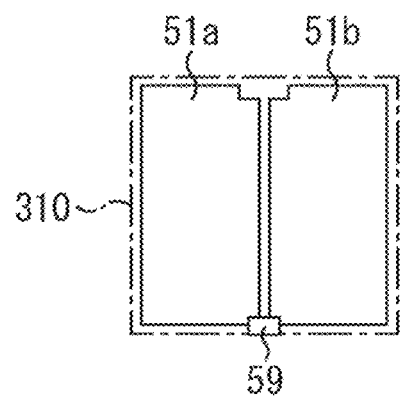

FIGS. 9A and 9B are views depicting a first different example of a pixel that can be adopted in the pixel substrate 30 (FIG. 4).

In particular, FIG. 9A is a circuit diagram depicting an example of a configuration of a pixel 310 as a first different example of a pixel that can be adopted in the pixel substrate 30, and FIG. 9B is a plan view depicting the example of the configuration of the pixel 310.

It is to be noted that, in FIGS. 9A and 9B, elements corresponding to those of FIG. 6 are denoted by identical reference signs, and description of them is suitably omitted in the following description.

Here, in a plane of the pixel 200 (FIGS. 5 and 6), the PD 51 occupies almost all of the area of the pixel 200. The size (magnitude) of the PD 51 is restricted by a distance over which an electron can move smoothly in the PD 51 from an end portion of the PD 51 to an entrance of the transfer Tr 55.

Therefore, in order that an electron can smoothly move in the PD, it is possible to provide, as appropriate, in a pixel to be adopted in the pixel substrate 30, a PD divisionally, i.e., to provide a plurality of PDs in a pixel. In a case where a plurality of PDs is provided in a pixel, various variations are available in a circuit configuration or a layout of pixels.

Further, it is necessary to carefully design the intensity of impurities of a semiconductor configuring a PD such that, for smooth drift of an electron in the PD, an appropriate potential gradient is provided in the depleted PD. In such a design, designing the intensity of impurities is easy for a PD of a rectangular shape in which the moving distance of an electron in one of the vertical direction and the horizontal direction is equal to or smaller than half the moving distance of an electron in the other direction, rather than for a PD of a square shape in which the moving distances of an electron in both the longitudinal direction and the lateral direction in a plane are equal to each other.

Therefore, it is possible to configure a pixel in a square shape by providing, in a pixel adopted in the pixel substrate 30, a plurality of PDs of a rectangular shape or to configure a pixel in a rectangular shape by providing a single PD of a rectangular shape in the pixel.

In FIGS. 9A and 9B, a pixel 310 includes two PDs 51a and 51b having an aspect ratio (longitudinal:lateral) of approximately 2:1 and is configured in a square shape by arranging the two PDs 51a and 51b side by side in the horizontal direction as depicted in FIG. 9B.

Referring to FIGS. 9A and 9B, the pixel 310 includes the PDs 51a and 51b, transfer Trs 55a and 55b, an amplification Tr 56, a reset Tr 57, and a detection node 58.

The pixel 310 is in common with the pixel 200 of FIG. 6 in that it includes the amplification Tr 56, reset Tr 57, and detection node 58. However, the pixel 310 is different from the pixel 200 of FIG. 6 in that it includes, in place of the PD 51 and the transfer Tr 55, the PDs 51a and 51b and the transfer Trs 55a and 55b.

The PD 51a is connected to the detection node 58 through the transfer Tr 55a, and the PD 51b is connected to the detection node 58 through the transfer Tr 55b. Accordingly, charge accumulated in the PD 51a is transferred to the detection node 58 through the transfer Tr 55a, and charge accumulated in the PD 51b is transferred to the detection node 58 through the transfer Tr 55b.

As a result, in the detection node 58, synthetic charge that is the sum of charge accumulated in the PD 51a and charge accumulated in the PD 51b is accumulated, and a pixel signal corresponding to the synthetic charge is outputted from the pixel 310.

In the pixel 310, a pixel Tr 59 can be disposed such that it is sandwiched between the PDs 51a and 51b as depicted in FIG. 9B. In FIGS. 9A and 9B, the transfer Trs 55a and 55b, amplification Tr 56, and reset Tr 57 configure the pixel Tr 59.

It is to be noted that the shape of the PDs 51a and 51b need not be a fully rectangular shape and may be deformed at an edge portion or the like thereof in accordance with the convenience in layout. Here, a shape of a longitudinally elongated or laterally elongated substantially rectangular shape in which the length of the long side is two times or more of that of the short side is referred to as a rectangular shape.

Figure 10:
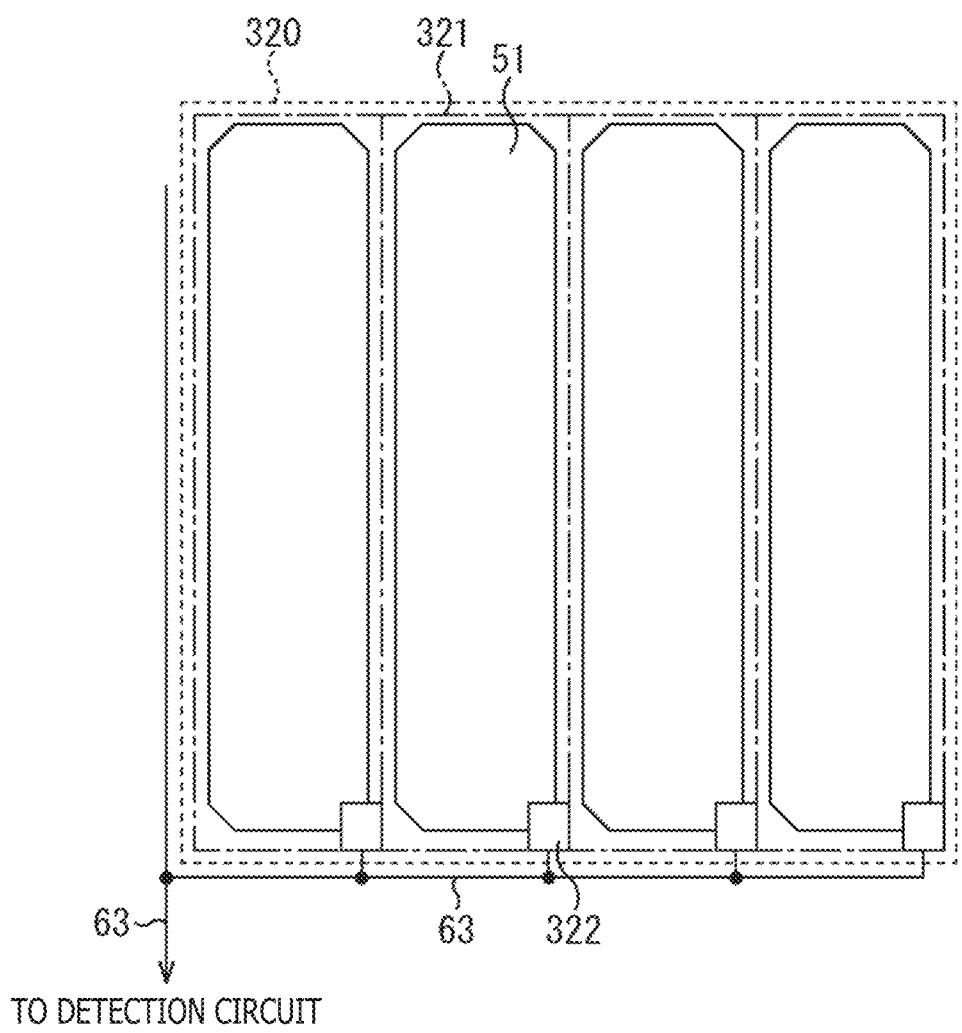
FIG. 10 is a view depicting a second different example of a pixel capable of being adopted in the pixel substrate 30.

FIG. 10 is a view depicting a second different example that can be adopted in the pixel substrate 30 (FIG. 4).

In particular, FIG. 10 is a plan view depicting an example of a configuration of a pixel 320 as the second different example of a pixel that can be adopted in the pixel substrate 30.

The pixel 320 includes four sub pixels 321 having an aspect ratio of approximately 4:1 and is configured in a square shape by arranging the four sub pixels 321 side by side in the lateral direction.

Each sub pixel 321 is configured similarly to the pixel 200 (FIG. 6). However, the planar shape of the PD 51 is not a square shape and is a rectangular shape having an aspect ratio of approximately 4:1.

Further, in the sub pixel 321, a pixel Tr 322 is disposed at the right lower corner. The pixel Tr 322 corresponds to the transfer Tr 55, amplification Tr 56, and reset Tr 57 of the pixel 200 (FIG. 6).

The output of the pixel Tr 322 of the four sub pixels 321 (source of the amplification Tr 56 (FIG. 6)) is connected to a vertical signal line 63, and the four sub pixels 321 simultaneously perform similar operation.

Accordingly, pixel signals read out by the pixel Trs 322 of the four sub pixels 321 are synthesized on the vertical signal line 63 and substantially averaged. Then, a signal obtained by the synthesis is supplied as a pixel signal of the pixel 320 to the detection circuit 33.

Although the pixel 310 of FIGS. 9A and 9B and the pixel 320 of FIG. 10 include a plurality of PDs of a rectangular shape, as a different pixel that can be adopted in the pixel substrate 30, for example, a pixel of a rectangular shape having one PD of a rectangular shape can be adopted.

Figure 11:
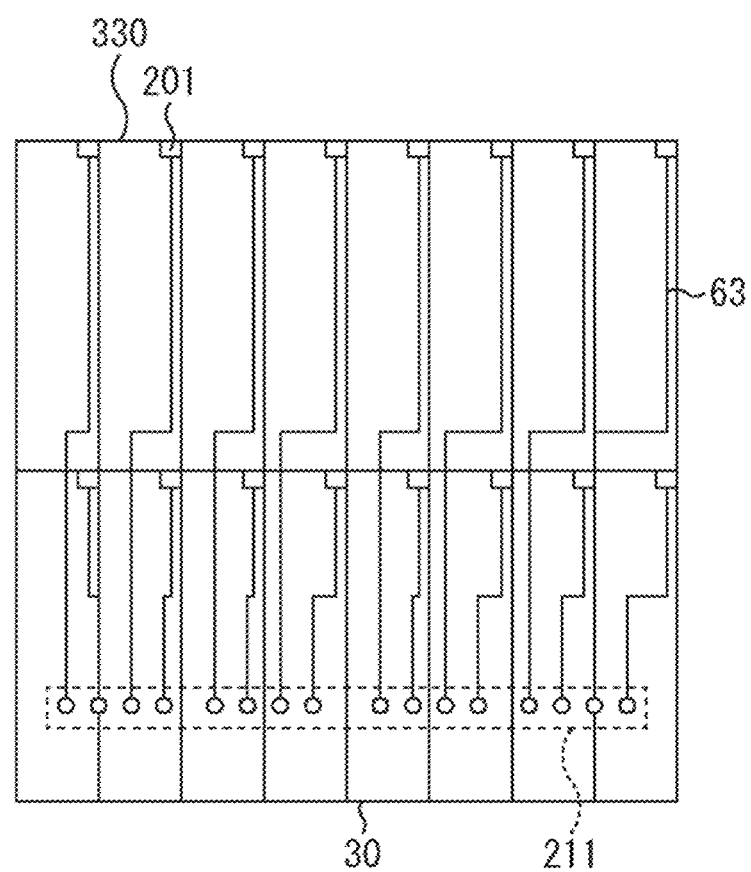
FIG. 11 is a view depicting a third different example of a pixel capable of being adopted in the pixel substrate 30.

FIG. 11 is a view depicting a third different example of a pixel that can be adopted in the pixel substrate 30 (FIG. 4).

In particular, FIG. 11 is a plan view of an example of a configuration of a pixel substrate 30 including a pixel 330 as the third different example of the pixel that can be adopted in the pixel substrate 30.

It is to be noted that, in FIG. 11, elements corresponding to those of FIG. 4 are denoted by identical reference signs, and description of them is suitably omitted in the following description.

Referring to FIG. 11, the pixel substrate 30 is configured similarly to that in the case of FIG. 4 except that it includes a pixel 330 of a rectangular shape in place of the pixel 200 of a square shape.

The pixel 330 is configured similarly to the pixel 200 (FIG. 6). However, the planar shape of the PD 51 is not a square shape and is a rectangular shape having an aspect ratio of approximately 4:1. Further, the planar shape of the pixel 330 is a rectangular shape similarly to the planar shape of the PD 51.

It is to be noted that, although, in FIG. 4, pixels 200 of a square shape are arranged in arrangement of 4×4 pixels on the pixel substrate 30, in FIG. 11, pixels 330 of a rectangular shape are arranged in arrangement of 8×2 pixels.

In FIG. 11, as in the case of FIG. 4, in the pixel 330, the pixel Tr 201 reads out a pixel signal, and the pixel signal is supplied to the detection circuit substrate 31 (FIG. 4) through the connection unit 211.

Figure 12:
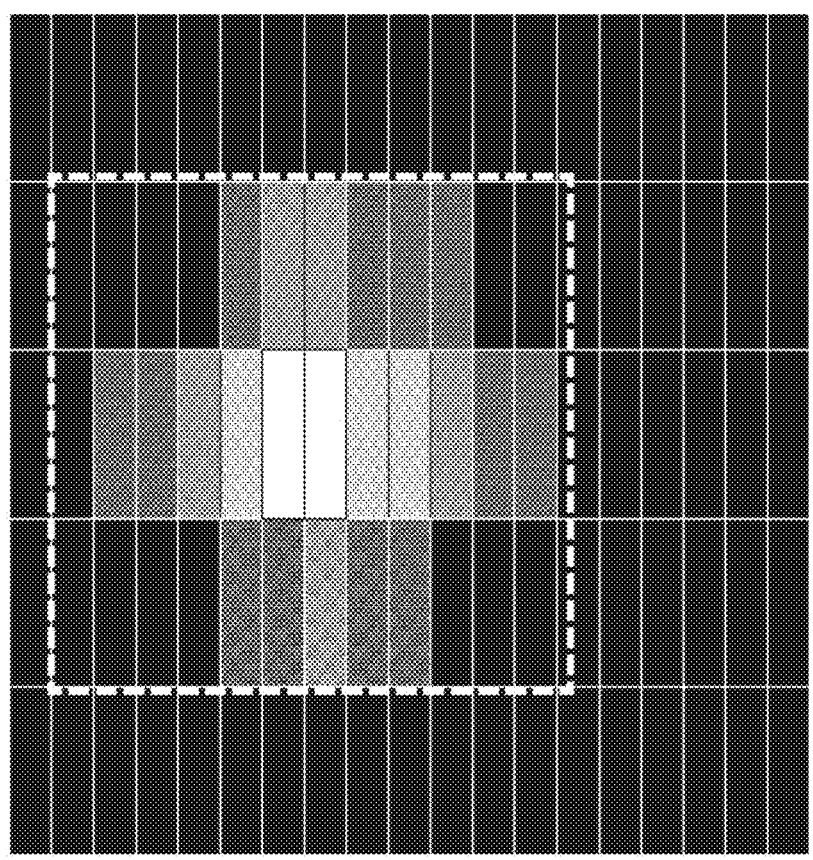
FIG. 12 is a plan view depicting an example of a pixel value of each pixel 300 obtained after A/D conversion of pixel signals of pixels 330 of the light detection block 22 in the photon count mode.

FIG. 12 is a plan view depicting, in a case where pixels 330 of a rectangular shape are formed on a pixel substrate 30, an example of pixel values (digital values of pixel signals) of pixels 300, which are obtained after A/D conversion of the pixel values of the pixels 330 of the light detection block 22, in the photon count mode.

It is to be noted that, in FIG. 12, a darker portion represents that a pixel value is low while a lighter portion represents that a pixel value is high, as in the case of FIG. 5.

Here, as described hereinabove with reference to FIG. 5, the logic compression circuit 34 determines a region of a plurality of pixels 330 (for example, a region surrounded by a broken line in FIG. 12) as a detection region, and scans the detection region with a pitch of the pixels 330 to detect peaks of the sum total of digital values of pixel signals of the pixels 330 in the detection region and then outputs positions of detection regions at which a peak of a predetermined value or more is obtained and the peaks, as data of bright spots arising from photons of an X-ray, i.e., as positions and energy of the bright spots.

Further, it is assumed that, for example, the long side of the pixel 330 is 100 μm long and the short side is 25 μm long and, as the detection region, a region of 300 μm square, i.e., a region of 12×3 pixels, is adopted.

Further, as the position of a bright spot, the position of the center of a detection region (at which a peak is obtained) is adopted.

In this case, a spatial resolution (x coordinate) of the position of the bright spot in the horizontal direction is a 25 μm distance equal to that of the short side of the pixel 330 and is high. However, the spatial resolution (y coordinate) of the position of the bright spot in the vertical direction is a 100 μm square equal to that of the long side of the pixel 330 and is low (coarse).

For the y coordinate in the vertical direction of the position of a bright spot at which the spatial resolution becomes low in the case where the position of the center of a detection region is used in this manner, it is desirable to adopt the y coordinate Yc of the center of gravity of the detection region, as described hereinabove with reference to FIG. 5. The y coordinate Yc of the center of gravity of the detection region can be determined in accordance with the expression (1) given hereinabove.

It is to be noted that, for the x coordinate of the position of a bright spot in the horizontal direction, it is also possible to adopt the position of the center of the detection region or adopt the x coordinate Xc of the position of the center of gravity of the detection region.

Further, although a region of 300 μm square is adopted as the detection region in the case described above, for the detection region, for example, a region of 4×1 pixels that is a smaller region of 100 μm square, a region of one pixel, or the like can be used instead.

In a case where a small region such as a region of 100 μm square smaller than a region of 300 μm square or a region of one pixel is adopted as the detection region, deeming the position of a bright spot determined using the small region as the detection region as the position of a detection region of 300 μm square, the position of the center of gravity of the detection region of 300 μm square is determined, and the y coordinate Yc of the position of the center of gravity can be acquired finally as the y coordinate in the vertical direction of the position of the bright spot. This similarly applies to the x coordinate of the position of the bright spot in the horizontal direction.

It is to be noted that, in the photon count mode, a bright spot can be detected by a given algorithm other than the algorithm of scanning a detection region and detecting a peak of the sum total of pixel values (digital values of pixel signals) in the detection region to detect a bright spot.

<Manufacturing Method of Detection Apparatus 12>

Figure 13:
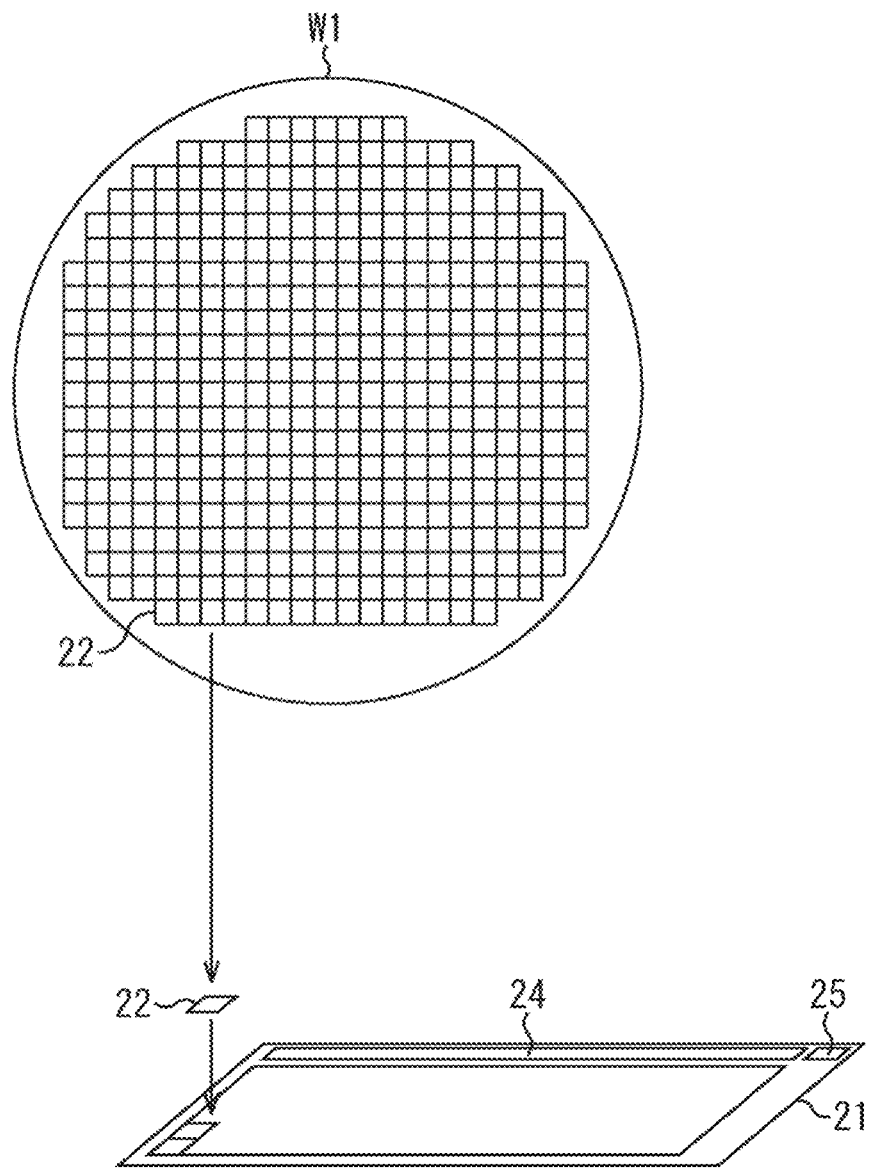
FIG. 13 is a view illustrating an outline of an example of a manufacturing method of a light sensor substrate 21 of the detection apparatus 12.

FIG. 13 is a view depicting an outline of an example of a manufacturing method of the light sensor substrate 21 of the detection apparatus 12.

A manufacturing apparatus, not depicted, for the detection apparatus 12 manufactures a large number, as a plurality, of light detection blocks 22 arranged side by side in an array on a silicon wafer W1 as a first semiconductor substrate, in accordance with a semiconductor manufacturing step. Further, the manufacturing apparatus performs a test of the light detection blocks 22 on the silicon wafer W1 and cuts out pieces of the light detection block 22 from the silicon wafer W1.

Further, the manufacturing apparatus manufactures the light sensor substrate 21 as a second semiconductor substrate on which the outputting circuit 24 and the timing controlling circuit 25 are formed.

Then, the manufacturing apparatus mounts the pieces of those light detection blocks 22 that are determined as allowable in the test in an array on the light sensor substrate 21 on which the outputting circuit 24 and the timing controlling circuit 25 are formed, and electrically connects the light sensor substrate 21 and the light detection block 22 to each other through a TSV (Though-Silicon Via) to complete the light sensor substrate 21.

By manufacturing the light detection block 22 separately from the light sensor substrate 21 and performing a test to select only the allowable light detection blocks 22 and then mounting the light detection blocks 22 on the light sensor substrate 21 in such a manner as described above, the detection apparatus 12 of a large area (at the face thereof that receives an X-ray) can be manufactured with a good yield.

<Different Embodiment of X-Ray Imaging Apparatus to which Present Technology is Applied>

Figure 14:
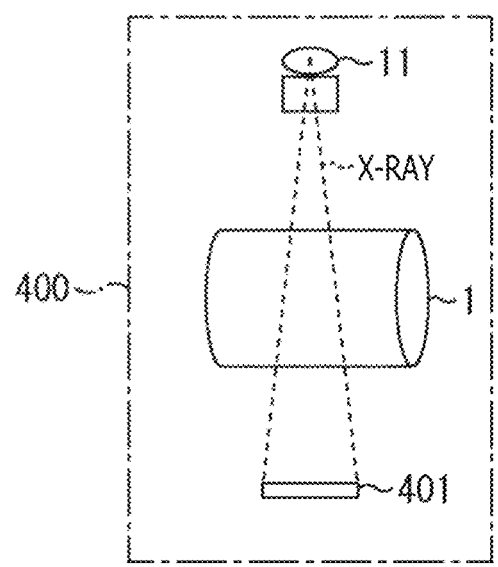
FIG. 14 is an overhead view depicting an example of a configuration according to another embodiment of an X-ray imaging apparatus to which the radiation detection apparatus of the present technology is applied.

FIG. 14 is an overhead view depicting an example of a configuration of a different embodiment of an X-ray imaging apparatus to which the radiation detection apparatus of the present technology is applied.

It is to be noted that, in FIG. 14, elements corresponding to those of FIG. 1 are denoted by identical reference signs, and description of them is suitably omitted in the following description.

Referring to FIG. 14, an X-ray imaging apparatus 400 includes the X-ray irradiation apparatus 11 and a detection apparatus 401.

Accordingly, the X-ray imaging apparatus 400 is in common with the X-ray imaging apparatus 10 of FIG. 1 in that it includes the X-ray irradiation apparatus 11.

However, the X-ray imaging apparatus 400 is different from the X-ray imaging apparatus 10 in that it includes the detection apparatus 401 in place of the detection apparatus 12.

The X-ray irradiation apparatus 11 and the detection apparatus 401 are disposed in an opposing relationship to each other with the subject 1 interposed therebetween.

The detection apparatus 401 is, for example, an FPD apparatus that detects an X-ray similarly to the detection apparatus 12 depicted in FIG. 1, and detects (photons of) an X-ray generated by the X-ray irradiation apparatus 11 and transmitted through the subject 1, and generates a two-dimensional projection image corresponding to the X-ray.

The X-ray imaging apparatus 400 has a transmission imaging mode and a tomographic imaging mode as imaging modes similarly to the X-ray imaging apparatus 10 depicted in FIG. 1.

<Example of Configuration of Detection Apparatus 401>

Figure 15:
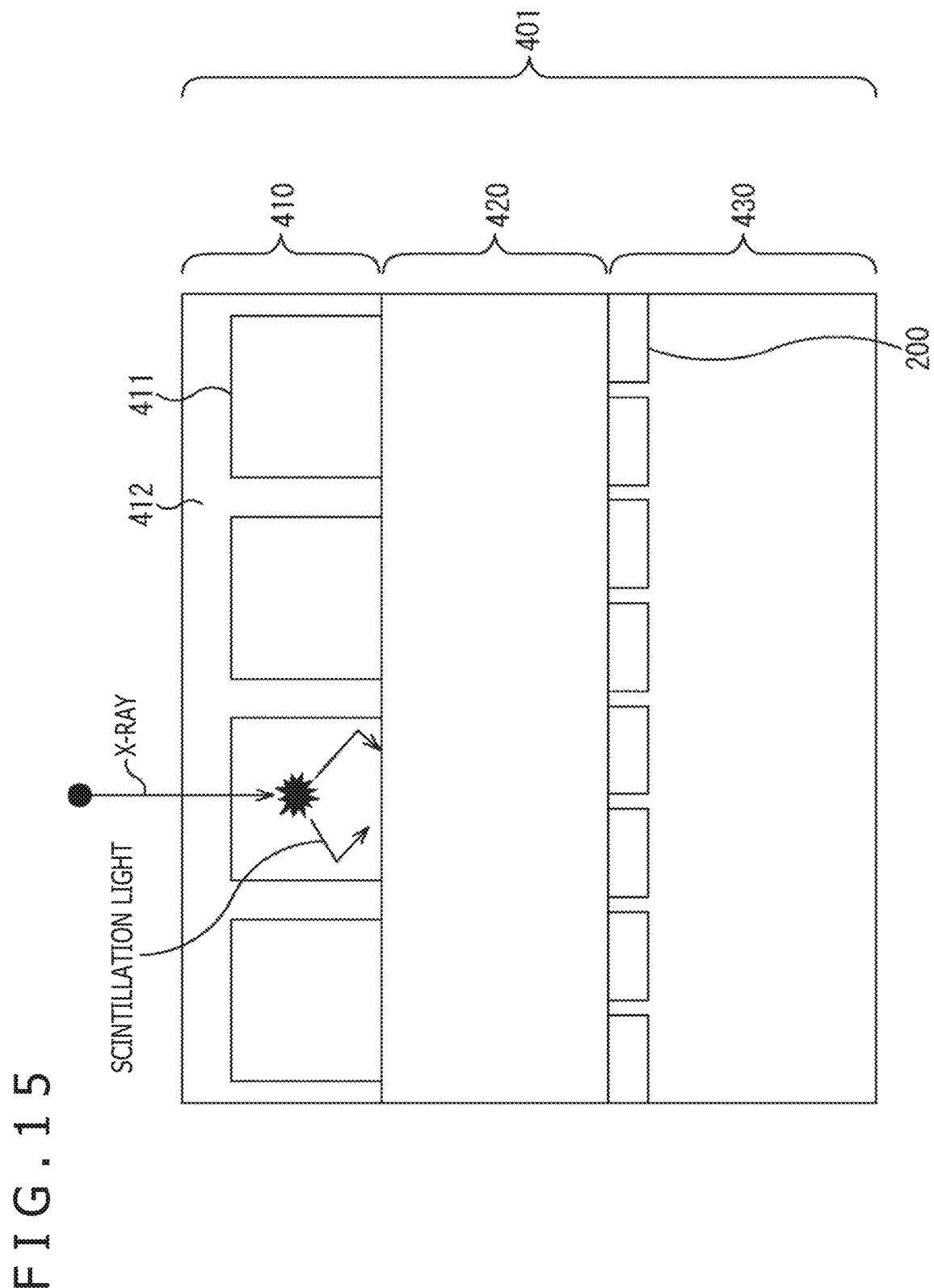
FIG. 15 is a sectional view depicting an example of a configuration of a detection apparatus 401.

FIG. 15 is a sectional view depicting an example of a configuration of the detection apparatus 401.

The detection apparatus 401 includes a plate-shaped scintillator plate 410, an FOP (Fiber Optic Plate) 420 and a light sensor substrate 430 disposed in this order, from the side on which an X-ray is incident (X-ray light receiving face side).

The scintillator plate 410 is a cell type scintillator in which a plurality of scintillator cells 411 is isolated from each other by a barrier wall 412 and disposed two-dimensionally in an array.

The scintillator plate 410 is configured such that a predetermined number, which is equal to or greater than 1, of pixels 200 the light sensor substrate 430 has are allocated to one scintillator cell 411.

Each scintillator cell 411 mainly includes a polycrystalline scintillator thin film including, for example, GOS (gadolinium oxysulfide) of columnar crystals. An X-ray incident on the scintillator cell 411 is converted into scintillation light that is visible light. The scintillation light formed by the conversion by the scintillator cell 411 is received by pixels 200 allocated to the scintillator cell 411.

The barrier wall 412 is formed such that it isolates a plurality of scintillator cells 411 arranged two-dimensionally in an array from each other (such that it surrounds each scintillator cell 411). Since the scintillator cells 411 are isolated from each other by the barrier wall 412, a bright spot arising from photons of an X-ray, i.e., a bright spot by scintillation light converted by the scintillator cell 411, is prevented from overlapping with a bright spot by scintillation light converted by any other scintillator cell 411.

Here, the shape of the plane of the scintillator cell 411 is a substantially rectangle, and as a size of the shape of the plane of the scintillator cell 411, 80 μm square or the like can be adopted, for example. Further, as the film thickness of the scintillator cell 411, 150 μm or the like can be adopted, for example.

Further, as the thickness of the barrier wall 412 (distance between adjacent ones of the plurality of scintillator cells 411 arranged two-dimensionally in an array), approximately 10 μm can be adopted, for example.

The FOP 420 is, for example, an optical device configured from a bundled optical fibers of lead glass and blocks an X-ray incident through the scintillator plate 410. Consequently, the FOP 420 suppresses the light sensor substrate 430 from being damaged by incidence of an X-ray. It is to be noted that the FOP 420 can also be provided in the detection apparatus 12 (FIG. 3).

The light sensor substrate 430 is configured similarly to the light sensor substrate 21 depicted in FIG. 3. Accordingly, the light sensor substrate 430 includes the light detection unit 23, outputting circuit 24, and timing controlling circuit 25 of FIG. 3 not depicted in FIG. 15.

Further, the light detection unit 23 includes a plurality of light detection blocks 22 arrayed two-dimensionally in an array as depicted in FIG. 3, and the light detection block 22 is configured such that a pixel substrate 30 having pixels 200 and so forth and a detection circuit substrate 31 having a detection circuits 33 and so forth are stacked as depicted in FIG. 4.

Here, for example, as the size of the shape of the plane of pixels 200 (arranged two-dimensionally in an array on a pixel substrate 30 not depicted in FIG. 15) the light sensor substrate 430 has, approximately 40 μm square can be adopted, for example.

In this case, by adopting approximately 80 μm square as the size of the shape of a plane of the scintillator cell 411 as described above, four pixels 200 of 2×2 pixels (vertical and horizontal) can be allocated to each scintillator cell 411.

Here, although, in the present embodiment, four pixels 200 of 2×2 pixels are allocated to each scintillator cell 411, the number of pixels 200 to be allocated to each scintillator cell 411 is not limited to four pixels of 2×2 pixels, and, for example, 1 pixel, 3×3 pixels, 2×3 pixels, and so forth can be adopted. In the following, unless otherwise specified, it is assumed that four pixels 200 of 2×2 pixels are allocated to each scintillator cell 411.

Figure 16:
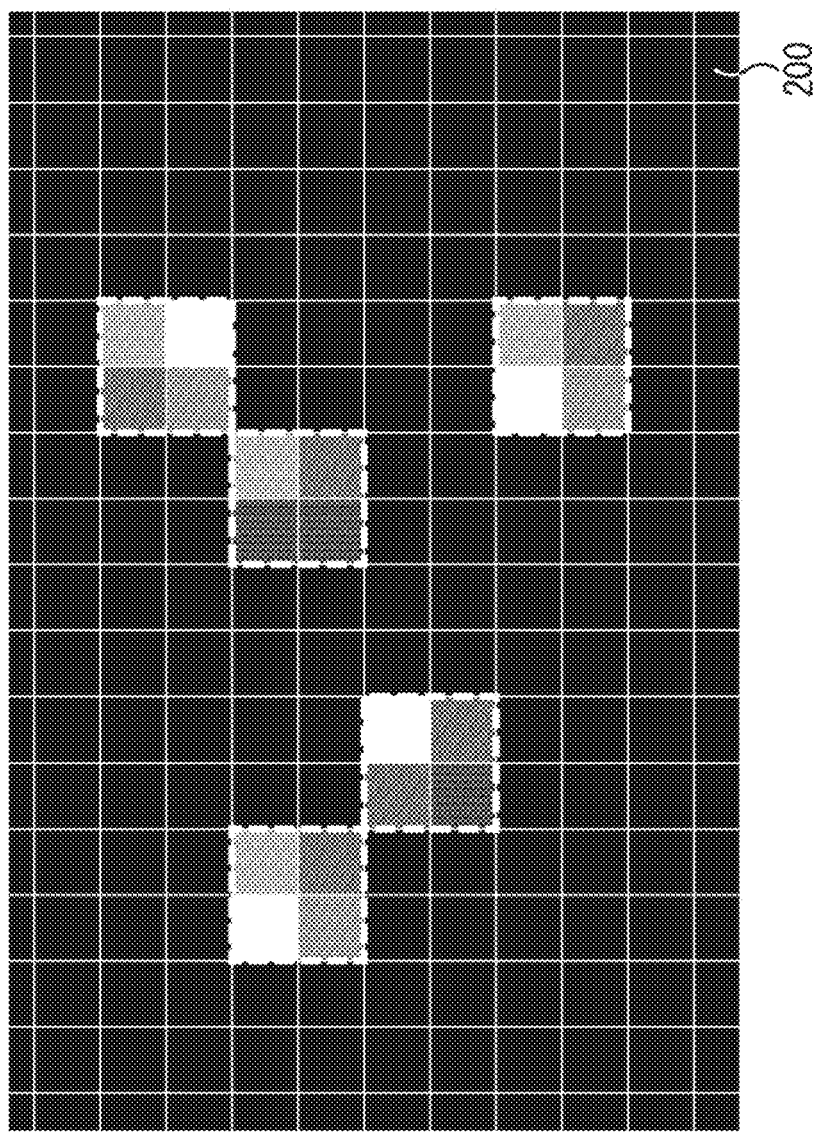
FIG. 16 is a plan view depicting an example of a pixel value of each pixel 200 obtained after A/D conversion of pixel signals of the pixels 200 of the light detection block 22 in the detection apparatus 401.

FIG. 16 is a plan view depicting an example of pixel values (digital values of pixel signals) of pixels 200 obtained after A/D conversion of the image signals of the pixels 200 of the light detection block 22 in the detection apparatus 401 of FIG. 15.

It is to be noted that, in FIG. 16, a darker portion represents that a pixel value is low while a lighter portion represents that a pixel value is high, as in the case of FIG. 5.

In FIG. 16, pixel values (digital values of pixel signals) of pixels 200 during a unit period of time for imaging in the case where imaging is performed in the photon count mode, i.e., during an exposure time for imaging of a projection image of one frame, are depicted.

Further, in FIG. 16, (regions of) bright spots arising from photons of X-rays in the case where five photons of X-rays are incident on different scintillator cells 411 are observed.

Here, a detection apparatus that adopts a scintillator plate that is not structured such that the scintillator cells 411 are isolated from each other by the barrier wall 412 and in which scintillation light is generated at a given position is referred to as a non-cell type detection apparatus.

If the dose of an X-ray is made high, then the number of photons of the X-ray becomes great and the number of bright spots arising from the photons of the X-ray becomes great. Accordingly, if the dose of the X-ray is made high, then, in a non-cell type detection apparatus, the possibility for (regions of) brightness spots to overlap with each other increases, and if bright spots overlap with each other, then it becomes possible to detect an X-ray, i.e., to determine an incident position of (a photon of) an individual X-ray incident on the non-cell type detection apparatus.

Therefore, in a non-cell type detection apparatus, it is necessary to make, in the photon count mode, the dose of X-rays a low dose to reduce the number of photons of the X-rays to perform capturing of a projection image. As a result, projection images of a large number of frames must be captured, and time is required to obtain necessary projection images.

On the other hand, in the detection apparatus 401, since the scintillator plate 410 has the scintillator cells 411 and the scintillator cells 411 are partitioned (isolated) from each other by the barrier wall 412, (the positions of) bright spots arising from photons of the X-rays are restricted within the range of the scintillator cell 411 (four pixels 200 of 2×2 pixels). Accordingly, even in the case where X-rays of a high dose are used, the X-rays can be detected accurately as long as a maximum of one photon of the X-rays is incident on one scintillator cell 411.

As described above, in the detection apparatus 401, since a bright spot arising from a photon of an X-ray is restricted within the range of the scintillator cell 411, it is prevented that a bright spot arising from a photon of an X-ray incident on a certain scintillator cell 411 and a bright spot arising from a photon of an X-ray incident on a different scintillator cell 411 overlap with each other. Accordingly, the detection apparatus 401 can accurately detect a photon of an individual X-ray incident as long as a maximum of one photon of an X-ray is incident on one scintillator cell 411.

It is to be noted that, according to a simulation performed by the inventor of the present technology, it was confirmed that, in the case where a high dose equal to approximately 10 times a dose with which overlapping of bright spots hardly occurs was used in a non-cell type detection apparatus, such a situation that a plurality of photons of an X-ray was incident on one scintillator cell 411 scarcely occurred.

Accordingly, with the detection apparatus 401, (a photon of) an individual X-ray can be detected among X-rays of a high dose equal to approximately 10 times a dose that is used in a non-cell type detection apparatus. Further, in the case where the detection apparatus 401 uses a high dose equal to approximately 10 times a dose that is used in a non-cell type detection apparatus, the capturing time for a projection image can be reduced to approximately ¹⁄₁₀ times that of a non-cell type detection apparatus, and a captured image can be obtained in a short period of time.

From the foregoing, with the detection apparatus 401, the diagnosis time can be reduced, for example, in diagnosis in which X-rays are used in a medical institution.

Figure 17:
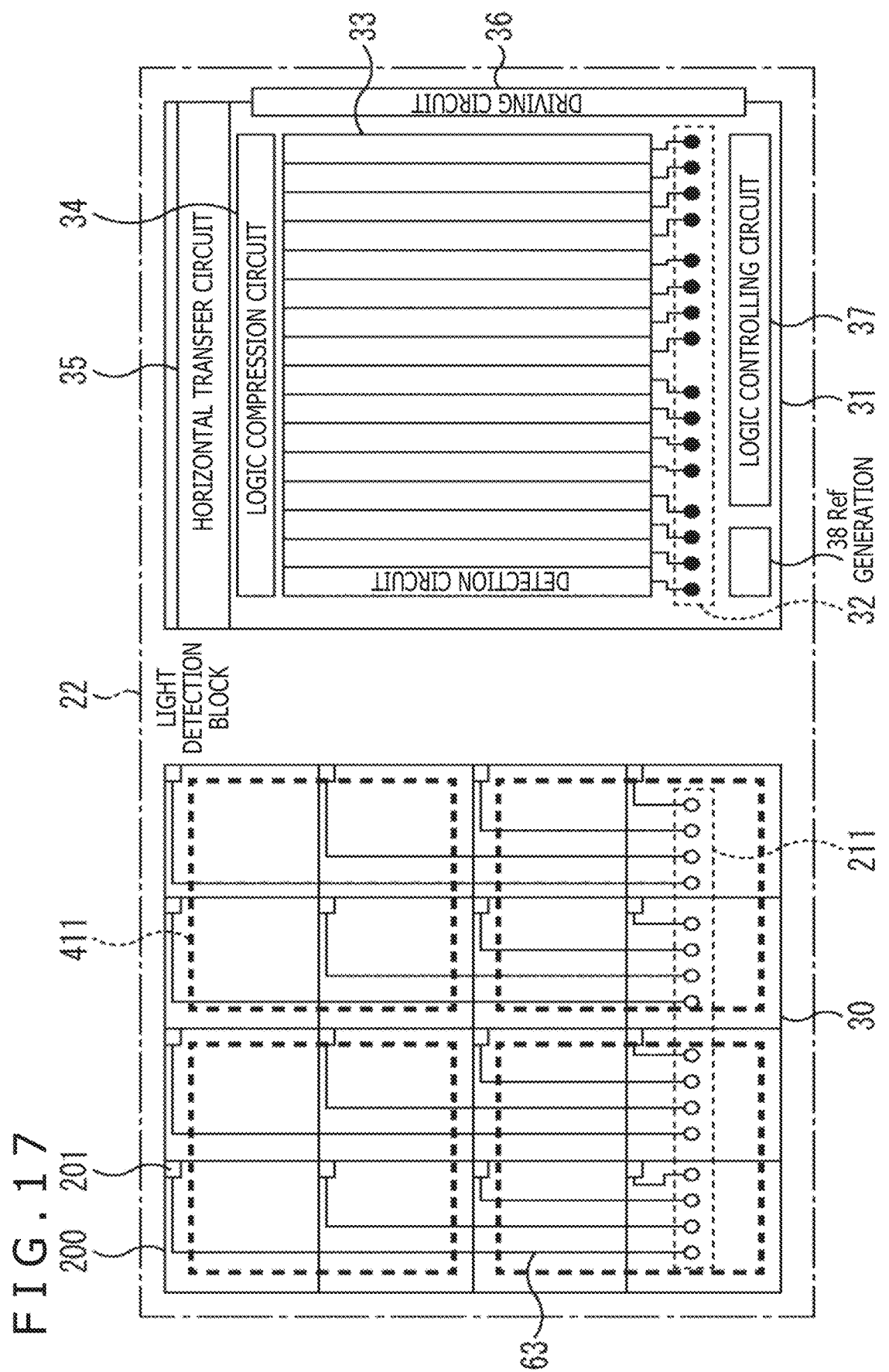
FIG. 17 is a plan view illustrating compression by a logic compression circuit 34 of the light detection block a light sensor substrate 430 has in the detection apparatus 401.

FIG. 17 is a plan view illustrating compression by the logic compression circuit 34 of the light detection block 22 the light sensor substrate 430 has in the detection apparatus 401 of FIG. 15.

In FIG. 17, the pixel substrate 30 and the detection circuit substrate 31 are not depicted in a stacked state and the pixel substrate 30 and the detection circuit substrate 31 are depicted in plan views, as in FIG. 4.

As depicted in FIG. 17, in the detection apparatus 401, four pixels 200 of 2×2 pixels are allocated to each scintillator cell 411.

If (a photon of) an X-ray is incident on a certain scintillator cell 411, then the scintillator cell 411 emits scintillation light. The scintillation light emitted from the scintillator cell 411 is received by one or more of the four pixels 200 of 2×2 pixels allocated to the scintillator cell 411, and a pixel signal corresponding to the received light amount of the scintillation light is A/D converted into a digital value by the detection circuits 33. The digital value of the pixel signal obtained by the detection circuits 33 is supplied to the logic compression circuit 34.

The logic compression circuit 34 performs compression of the digital value of the pixel signal from the detection circuits 33.

Here, as described hereinabove with reference to FIG. 16, in the detection apparatus 401, since the bright spot arising from the photon of the X-ray incident on the scintillator cell 411 is restricted within the range of the scintillator cell 411, the logic compression circuit 34 can perform compression of a digital value of a pixel signal by, for example, taking four pixels 200 of 2×2 pixels allocated to one scintillator cell 411 as one unit.

In particular, for example, the logic compression circuit 34 adds digital values of pixel signals of four pixels 200 of 2×2 pixels of one unit and outputs a sum value obtained as a result of the addition as a pixel value of one unit.

In this case, if it is assumed that a digital value of a pixel signal of one pixel 200 is represented by 10 bits, 4 (pixels)×10 (bits)=40 bits representing a digital value of pixel signals for one unit, i.e., for four pixels 200 of 2×2 pixels, are compressed into a pixel value of 12 bits.

Further, for example, the logic compression circuit 34 detects a pixel 200 the digital value of whose pixel signal is maximum among the four pixels 200 of 2×2 pixels of one unit allocated to the scintillator cell 411. Then, the logic compression circuit 34 selects the position of the pixel 200 the digital value of which is maximum among the positions of the four pixels 200 of 2×2 pixels of one unit as an incident position (of a photon) of the X-ray and outputs position information of 2 bits representative of the incident position of the X-ray among the positions of the four pixels 200 of 2×2 pixels of one unit. Consequently, the logic compression circuit 34 compresses the positions of the pixels of the four pixels 200 of 2×2 pixels into a position of one pixel 200, in a sense.

In the case where the logic compression circuit 34 outputs position information of 2 bits representative of an incident position, 4×10=40 bits that are a digital value of pixel signals of four pixels 200 of 2×2 pixels allocated to a scintillator cell 411 are compressed into data of a bright spot arising from a photon of an X-ray, which is represented by the total of an addition value of 12 bits obtained by adding digital values of pixel signals of four pixels 200 of 2×2 pixels and position information of 2 bits, i.e., by 14 bits.

From the foregoing, the data amount of data representative of a projection image to be outputted from the detection apparatus 401 can be reduced by the logic compression circuit 34, and data for a projection image of one frame can be outputted in a short period of time, for example. Accordingly, it is possible to perform high speed imaging and obtain a projection image of a radiation in a short period of time.

Here, the logic compression circuit 34 can perform any compression in addition to or in place of the compression described above.

Also in the case where an X-ray of a high dose is used in the photon count mode as described hereinabove with reference to FIG. 16, pixel signals outputted from many pixels 200 in the detection apparatus 401 are dark pixel signals that include noise.

Accordingly, if a threshold value process is performed by the logic compression circuit 34 for a digital value of a pixel signal of each pixel 200 outputted from each detection circuit 33 as described hereinabove with reference to FIG. 5 and any digital value of a pixel equal to or lower than the threshold value is deemed as fully dark (zero), the digital values of pixel signals of many pixels 200 become 0.

Since it is possible to significantly reduce the data amount of such data including many zeros by given compression and to output data in a shorter period of time, it is very effective to perform given compression in the logic compression circuit 34.

It is to be noted that, although, in the present embodiment, compression of digital values of pixel signals is performed in the inside of the light sensor substrate 430, the compression of digital values of pixel signals may otherwise be performed outside the light sensor substrate 430.

As described above, since the scintillator cells 411 in the detection apparatus 401 are isolated from each other by the barrier wall 412, a bright spot arising from a photon of an X-ray, i.e., a bright spot by scintillation light converted by a scintillator cell 411, can be prevented from overlapping with a bright spot by scintillation light converted by a different scintillator cell 411.

Accordingly, in the detection apparatus 401, even in the case where an X-ray of a high dose is used, a photon of each incident X-ray can be detected accurately as long as a maximum of one photon of an X-ray is incident on one scintillator cell 411.

Consequently, in the detection apparatus 401, a higher dose than that in a non-cell type detection apparatus can be used in the photon count mode, and a projection image of a radiation can be obtained in a short period of time.

Further, since the logic compression circuit 34 performs compression of digital values of pixel signals in such a manner as described above, the data amount of data for a projection image to be outputted from the detection apparatus 401 can be reduced, and, for example, data for a projection image of one frame can be outputted in a short period of time. Accordingly, it is possible to achieve high speed imaging and obtain a projection image of a radiation in a short period of time.

<Example of Configuration of X-Ray Imaging System to which Technology According to Present Disclosure can be Applied>

Figure 18:
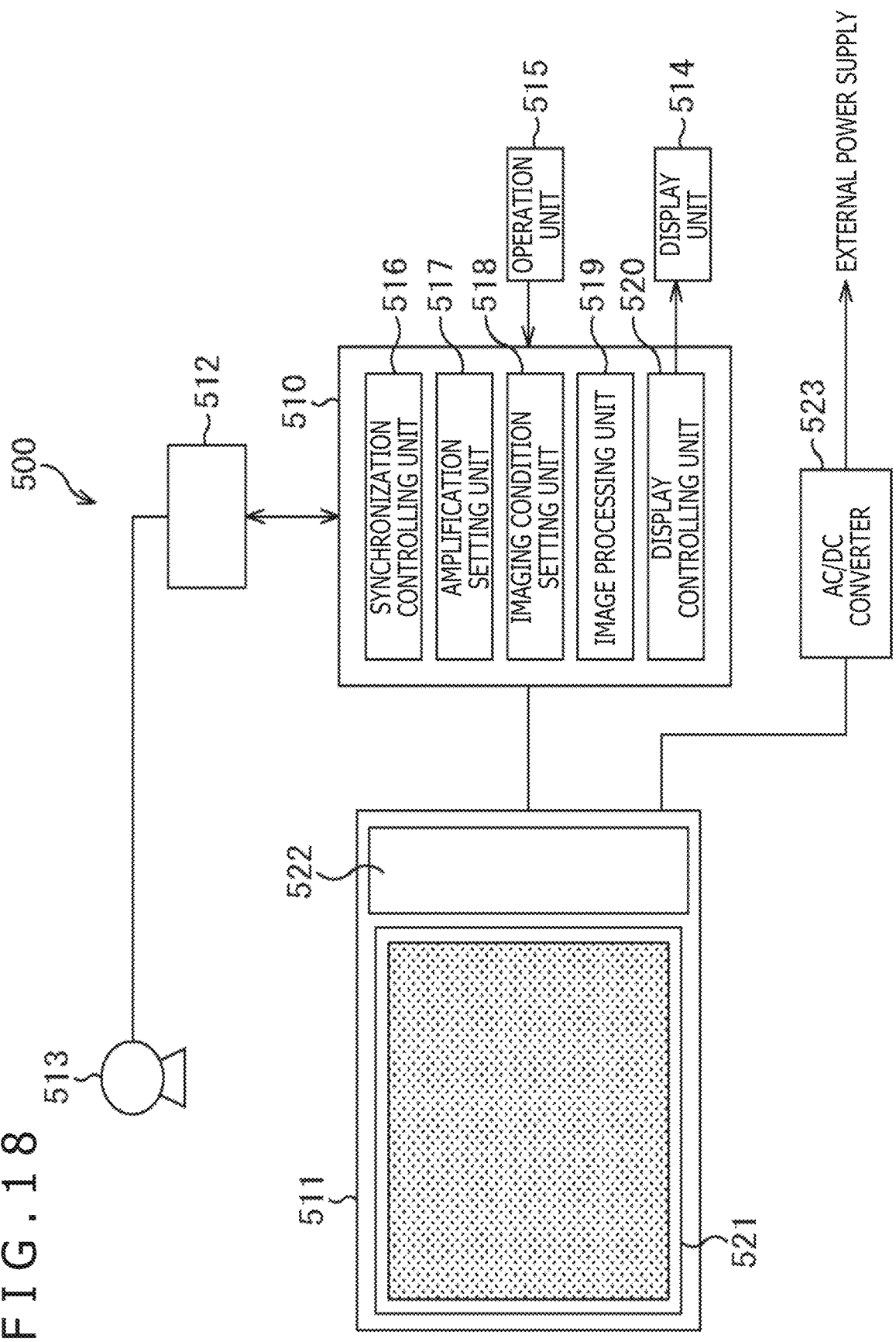
FIG. 18 is a block diagram illustrating an example of a configuration of an X-ray imaging system to which the technology according to the present disclosure can be applied.

FIG. 18 is a block diagram illustrating an example of a configuration of an X-ray imaging system to which the technology according to the present disclosure can be applied.

An X-ray imaging system 500 includes a control apparatus 510, an imaging apparatus 511, an X-ray generation apparatus 512, an X-ray tube 513, a display unit 514, an operation unit 515, and an AC/DC converter 523. The X-ray imaging system 500 is, for example, a round-trip car, a C arm, a CT imaging system, or the like.

The control apparatus 510 executes control of the entire system. The control apparatus 510 includes a synchronization controlling unit 516, an amplification setting unit 517, an imaging condition setting unit 518, an image processing unit 519, and a display controlling unit 520. The imaging condition setting unit 518 gives instructions on the imaging conditions to the imaging apparatus 511 and the X-ray generation apparatus 512 on the basis of an order input from the operation unit 515 or the outside.

The synchronization controlling unit 516 performs synchronization control of synchronizing X-ray irradiation of the X-ray tube 513 and X-ray reception and reading out of the imaging apparatus 511 with each other in response to depression of an irradiation switch not depicted. The synchronization control is performed, for example, by sending a pulse signal to the imaging apparatus 511 and the X-ray generation apparatus 512. By the synchronization control, the X-ray generation apparatus 512 causes the X-ray tube 513 to generate an X-ray at a predetermined timing. A captured image obtained by the imaging apparatus 511 in response to the generated X-ray is sent to the control apparatus 510.

The captured image is displayed on the display unit 514 by the display controlling unit 520 after predetermined processing by the image processing unit 519. Outputting of an image is executed successively by a plural number of times under the control of the control apparatus 510 to execute moving picture imaging, and still picture imaging is executed by single time capturing.

The amplification setting unit 517 performs setting for controlling an activation timing of pixel amplifiers included in the image sensor of the imaging apparatus 511. The pixel amplifier is set such that it is activated when an electric signal generated by a photoelectric conversion element is to be sent to a sample hold circuit, but is not activated in any other case. Further, the activation timing of amplifiers is set individually for each partial region of the image sensor. The setting relating to control of the pixel amplifier is performed by at least one of an input from the operation unit 515, information reception from an external apparatus and setting information stored in a memory, not depicted, in the control apparatus 510.

The imaging apparatus 511 principally includes an image sensor 111 and an imaging controlling unit 522 for controlling the sensor. The imaging apparatus 511 is, for example, a flat panel detector or an X-ray detector used for X-ray imaging. By converting an X-ray into visible light by a phosphor not depicted and receiving the visible light by an image sensor 521 to generate charge, an X-ray image according to a dose distribution of X-rays arriving at the imaging apparatus 511 can be obtained.

An example of the X-ray imaging system 500 to which the technology according to the present disclosure can be applied has been described above. The technology according to the present disclosure can be applied to the imaging apparatus 511 among the configurations described above. In particular, the detection apparatuses 12 and 401 can be applied to the imaging apparatus 511. By applying the technology according to the present disclosure to the imaging apparatus 511, a projection image of a radiation can be obtained in a short period of time.

<Example of Sectional Configuration of Solid-State Imaging Device Capable of being Applied to Technology According to Present Disclosure>

Figure 19:
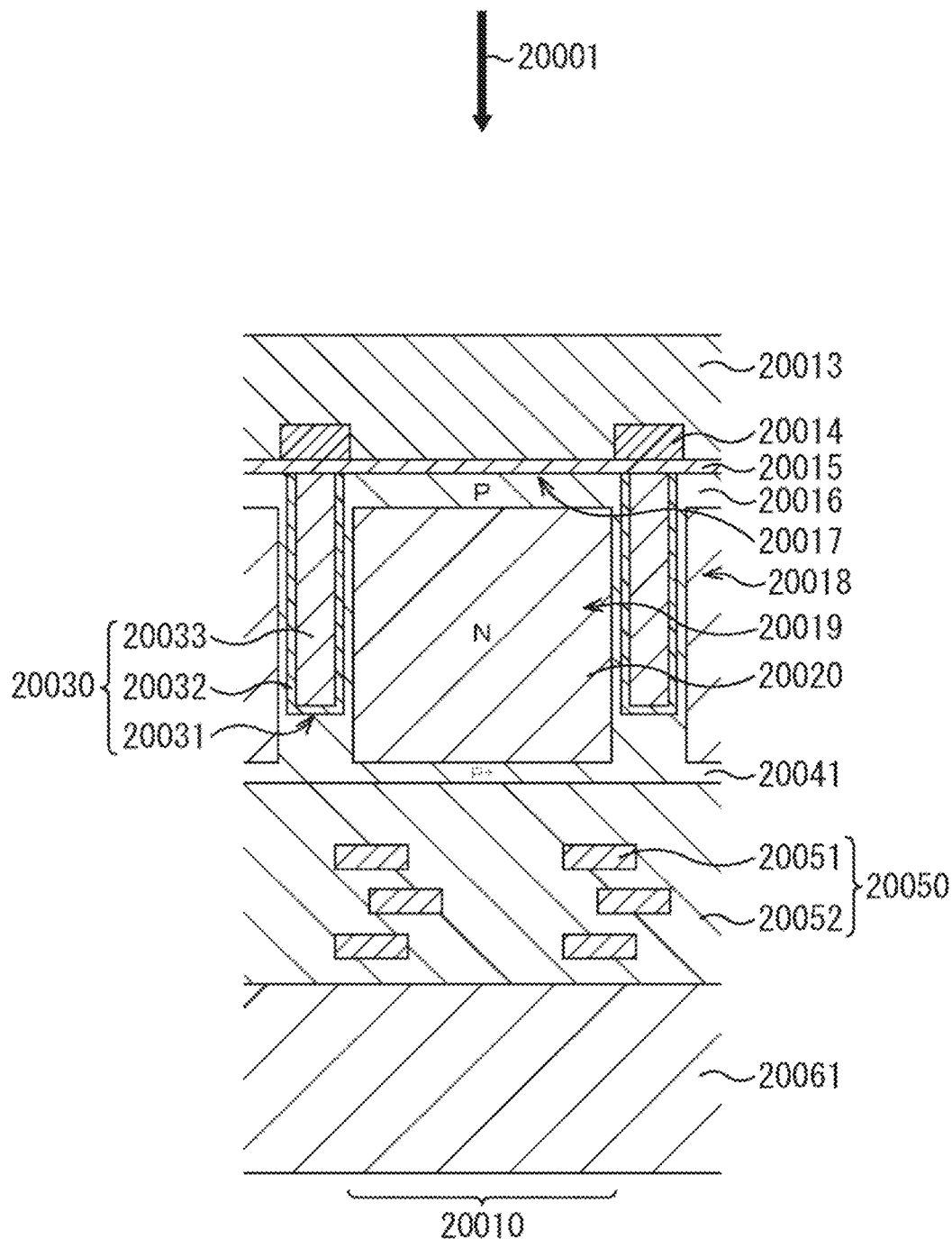
FIG. 19 is a sectional view depicting an example of a configuration of a solid-state imaging apparatus capable of being applied to the technology according to the present disclosure.

FIG. 19 is a sectional view depicting an example of a configuration of a solid-state imaging device capable of being applied to the technology according to the present disclosure.

In the solid-state imaging device, a PD (Photodiode) 20019 receives incident light 20001 incident from a rear face (in FIG. 19, from an upper face) side of a semiconductor substrate 20018. An flattening film 20013 is provided above the PD 20019, and the incident light 20001 incident through the flattening film 20013 is received by a light receiving face 20017 and subjected to photoelectric conversion.

For example, in the PD 20019, an n-type semiconductor region 20020 is formed as a charge accumulation region for accumulating charge (electrons). In the PD 20019, the n-type semiconductor region 20020 is provided in the inside of p-type semiconductor regions 20016 and 20041 of the semiconductor substrate 20018. On a front face (lower face) side of the semiconductor substrate 20018 in the n-type semiconductor region 20020, the p-type semiconductor region 20041 having a higher impurity intensity than that on the rear face (upper face) side is provided. In short, the PD 20019 has a HAD (Hole-Accumulation Diode) structure, and the p-type semiconductor regions 20016 and 20041 are formed such that dark current is suppressed from being generated in interfaces of the upper face side and the lower face side of the n-type semiconductor region 20020.

In the inside of the semiconductor substrate 20018, a pixel isolation unit 20030 for electrically isolating a plurality of pixels 20010 is provided, and the PD 20019 is provided in each of the regions partitioned by the pixel isolation unit 20030. In FIG. 19, when the solid-state imaging device is viewed from the upper face side, the pixel isolation unit 20030 is, for example, formed in a lattice pattern such that it is interposed between a plurality of pixels 20010, and the PD 20019 is formed in each of the regions partitioned by the pixel isolation unit 20030.

In each PD 20019, the anode is grounded, and in the solid-state imaging device, signal charge (for example, electrons) accumulated in the PD 20019 is read out through a transfer Tr (MOS FET) or the like not depicted and is outputted as an electric signal to a VSL (vertical signal line) not depicted.

A wiring layer 20050 is provided on a front face (lower face) of the semiconductor substrate 20018 on the opposite side to a rear face (upper face) on which a light shielding film 20014 is provided.

The wiring layer 20050 includes a wiring 20051 and an insulating layer 20052 and is formed such that the wiring 20051 is electrically connected to the elements in the insulating layer 20052. The wiring layer 20050 is what is generally called a multilayer wiring layer, in which an interlayer insulating film configuring the insulating layer 20052 and the wiring 20051 are layered alternately by a plural number of times. Here, as the wirings 20051, wirings to Trs for reading out charge from the PDs 20019 such as transfer Trs and wirings such as the VL are stacked with the insulating layer 20052 interposed therebetween.

A support substrate 20061 is provided on a face of the wiring layer 20050 on the opposite side to the side on which the PD 20019 is provided. For example, a substrate including a silicon semiconductor of a thickness of several hundred μm is provided as the support substrate 20061.

The light shielding film 20014 is provided on the rear face (in FIG. 19, on the upper face) side of the semiconductor substrate 20018.

The light shielding film 20014 is configured such that it blocks part of incident light 20001 directed from above the semiconductor substrate 20018 toward the rear face of the semiconductor substrate 20018.

The light shielding film 20014 is provided above the pixel isolation unit 20030 provided in the inside of the semiconductor substrate 20018. Here, the light shielding film 20014 is provided such that it protrudes in a projecting shape through an insulating film 20015 such as a silicon oxide film on the rear face (upper face) of the semiconductor substrate 20018. In contrast, above the PD 20019 provided in the inside of the semiconductor substrate 20018, the light shielding film 20014 is not provided but an opening is formed such that the incident light 20001 is incident on the PD 20019.

In particular, when the solid-state imaging device is viewed from the upper face side in FIG. 19, the planar shape of the light shielding film 20014 has a lattice pattern and openings through which the incident light 20001 passes to the light receiving face 20017 are formed.

The light shielding film 20014 includes a light blocking material that blocks light. For example, the light shielding film 20014 is formed by stacking a titanium (Ti) film and a tungsten (W) film alternately. Otherwise, the light shielding film 20014 can be formed, for example, by stacking a titanium nitride (TiN) film and a tungsten (W) film sequentially.

The light shielding film 20014 is coated with the flattening film 20013. The flattening film 20013 is formed using an insulating material that transmits light.

The pixel isolation unit 20030 includes a grooved portion 20031, a fixed charge film 20032, and an insulating film 20033.

The fixed charge film 20032 is formed such that it covers the grooved portion 20031, which partitions the plurality of pixels 20010 from each other, on the rear face (upper face) side of the semiconductor substrate 20018.

In particular, the fixed charge film 20032 is provided so as to coat the inner side face of the grooved portion 20031 formed on the rear face (upper face) side of the semiconductor substrate 20018 with a fixed thickness. Then, the insulating film 20033 is provided (filled) such that it fills up the inside of the grooved portion 20031 coated with the fixed charge film 20032.

Here, the fixed charge film 20032 is formed using a high dielectric having negative fixed charge such that a positive charge (hole) accumulation region is formed at an interface portion thereof with the semiconductor substrate 20018 to suppress generation of dark current. Since the fixed charge film 20032 is formed so as to have negative fixed charge, an electric field is applied to the interface with the semiconductor substrate 20018 by the negative fixed charge to form the positive charge (hole) accumulation region.

The fixed charge film 20032 can include, for example, a hafnium oxide film (HfO2 film). Further, the fixed charge film 20032 can be formed so as to otherwise include at least one of oxides of hafnium, zirconium, aluminum, tantalum, titanium, magnesium, yttrium, and lanthanoid element, for example.

Such a solid-state imaging device as described above can be applied to the light detection block 22 of the detection apparatus 12 or the detection apparatus 401.

Although the radiation detection apparatus of the present technology has been described in connection with a case in which it is applied to the X-ray imaging apparatus 10 that detects an X-ray, the present technology can be applied to an apparatus that detects not only an X-ray but also a given radiation such as alpha rays, for example. Further, the present technology can be applied to X-ray inspection and so forth that are used, for example, for detection or scientific measurement of cosmic rays, for CT for industrial use, for security, and so forth.

Further, the embodiment of the present technology is not limited to the embodiment described hereinabove and can be changed variously without departing from the subject matter of the present technology.

Furthermore, the advantageous effects described in the present specification are only exemplary and are not restrictive, and other advantageous effects may be applicable.

It is to be noted that the present technology can assume the following configuration.

<1>
A radiation detection apparatus, including:
a scintillator that emits scintillation light in response to incidence of a radiation;
a pixel substrate on which a plurality of pixels each of which photoelectrically converts the scintillation light and outputs a pixel signal according to a light amount of the scintillation light is disposed in an array;
a detection circuit substrate that includes an A/D (Analog to Digital) conversion unit for A/D converting the pixel signal and is stacked on the pixel substrate; and
a compression unit that compresses digital data outputted from the A/D conversion unit.

<2>
The radiation detection apparatus according to <1>, in which
the scintillator includes a cell type scintillator in which a plurality of scintillator cells is arranged in an array and isolated from each other by a barrier wall; and
one or more pixels are allocated to each of the scintillator cells.

<3>
The radiation detection apparatus according to <2>, in which
two or more pixels are allocated to each of the scintillator cells; and
the compression unit adds the digital data of the two or more pixels allocated to the scintillator cell to compress the digital data.

<4>
The radiation detection apparatus according to <2>, in which
two or more pixels are allocated to each of the scintillator cells; and
the compression unit selects a position of the pixel whose digital data is maximum from among positions of the two or more pixels allocated to the scintillator cell, as an incident position of the radiation.

<5>
The radiation detection apparatus according to <2>, in which
two or more pixels are allocated to each of the scintillator cells; and
the compression unit adds the digital data of the two or more pixels allocated to the scintillator cell to compress the digital data and selects a position of the pixel whose digital data is maximum from among positions of the two or more pixels allocated to the scintillator cell, as an incident position of the radiation.

<6>
The radiation detection apparatus according to any one of <1> to <5>, in which
a plurality of light detection blocks each including the pixel board and the detection circuit board stacked with each other is arranged in an array.

<7>
The radiation detection apparatus according to <6>, in which
the light detection blocks include the compression unit.

<8>
The radiation detection apparatus according to <6> or <7>, in which
the radiation detection apparatus is manufactured by
forming a plurality of the light detection blocks on a first semiconductor substrate;

cutting out pieces of the light detection blocks from the first semiconductor substrate; and
arranging a plurality of pieces of the light detection blocks in an array on a second semiconductor substrate.

<9>
The radiation detection apparatus according to any one of <1> to <8>, further including:
a radiation generation unit that is disposed at a position sandwiching a subject and generates the radiation.

<10>
The radiation detection apparatus according to any one of <1> to <9>, in which
the pixel has a PD (Photodiode) having a substantially rectangular planar shape whose long side is equal to or longer than twice the short side.

<11>
The radiation detection apparatus according to <10>, in which
the pixel has a plurality of PDs having the substantially rectangular planar shape whose long side is equal to longer than twice the short side.

<12>
The radiation detection apparatus according to any one of <1> to <11>, further including:
an adjustment mechanism that adjusts a quantization width of the A/D conversion to a quantization width corresponding to the pixel signal of less than one electron or hole or to a quantization width corresponding to the pixel signal of one or more electrons or holes.

<13>
The radiation detection apparatus according to <12>, in which
the A/D conversion unit includes
a comparator that compares a reference signal that changes with a predetermined inclination and the pixel signal with each other and outputs a result of the comparison between the reference signal and the pixel signal, and
a counter that counts a period of time until a relationship in magnitude between the reference signal and the pixel signal reverses, in response to the result of the comparison and outputs a count value; and
an amplifier that amplifies the pixel signal to be supplied to the comparator and has an adjustable gain is provided as the adjustment mechanism.

<14>
The radiation detection apparatus according to <12>, in which
the A/D conversion unit includes
a comparator that compares a reference signal that changes with a predetermined inclination and the pixel signal with each other and outputs a result of the comparison between the reference signal and the pixel signal, and
a counter that counts a period of time until a relationship in magnitude between the reference signal and the pixel signal reverses, in response to the result of the comparison and outputs a count value; and
a reference signal generation unit that generates the reference signal and is capable of adjusting the inclination of the reference signal is provided as the adjustment mechanism.

<15>
The radiation detection apparatus according to <12>, in which
the A/D conversion unit includes a comparator that compares a reference signal that changes with a predetermined inclination and the pixel signal with each other and outputs a result of the comparison between the reference signal and the pixel signal, and
a counter that counts a period of time until a relationship in magnitude between the reference signal and the pixel signal reverses, in response to the result of the comparison and outputs a count value; and
the pixel has, as the adjustment mechanism, a gain adjustment unit that adjusts a gain of the pixel signal to be supplied to the comparator.

REFERENCE SIGNS LIST

1 Subject, 10 X-ray imaging apparatus, 11 X-ray irradiation apparatus, 12 Detection apparatus, 20 Scintillator plate, 21 Light sensor substrate, 22 Light detection block, 23 Light detection unit, 24 Outputting circuit, 25 Timing controlling circuit, 30 Pixel substrate, 31 Detection circuit substrate, 32 Connection unit, 33 Detection circuit, 34 Logic compression circuit, 35 Horizontal transfer circuit, 36 Driving circuit, 37 Logic controlling circuit, 38 Reference signal generation circuit, 51, 51$a$, 51$b$ PD, 52 Accumulation node, 53 Power supply line, 55, 55$a$, 55$b$ Transfer Tr, 56 Amplification Tr, 57 Reset Tr, 58 Detection node (FD), 59 Pixel Tr, 60 Row driving unit, 61 Constant current source, 62 Signal detection unit, 63 Vertical signal line, 70 Amplification circuit, 71 Capacitor, 72 Amplifier, 73 Variable capacitor, 80 A/D converter, 81, 82 Capacitor, 83 Comparator, 84 Counter, 85 Reference signal line, 101 Circuit, 200 Pixel, 201 Pixel Tr, 211 Connection unit, 310, 320 Pixel, 321 Sub pixel, 330 Pixel, 400 X-ray imaging apparatus, 401 Detection apparatus, 410 Scintillator plate, 411 Scintillator cell, 412 Barrier wall, 420 FOP, 430 Light sensor substrate, 500 X-ray imaging system, 510 Control apparatus, 511 Imaging apparatus, 512 X-ray generation apparatus, 513 X-ray tube, 514 Display unit, 515 Operation unit, 516 Synchronization controlling unit, 517 Amplification setting unit, 518 Imaging condition setting unit, 519 Image processing unit, 520 Display controlling unit, 521 Image sensor, 522 Imaging controlling unit, 523 AC/DC converter

The invention claimed is:
1. A radiation detection apparatus, comprising:
a scintillator configured to emit scintillation light based on incidence of a radiation;
a pixel substrate comprising an array of a plurality of pixels,
wherein each pixel of the plurality of pixels is configured to:
photoelectrically convert the scintillation light; and
output a pixel signal based on the photoelectric conversion of a light amount of the scintillation light;
a detection circuit substrate comprising an Analog to Digital (A/D) conversion unit configured to:
A/D convert the pixel signal; and
output digital data for the pixel signal of each pixel of the plurality of pixels,
wherein the detection circuit substrate is stacked on the pixel substrate;
an adjustment mechanism configured to adjust a quantization width of the A/D conversion, wherein the quantization width of the A/D conversion is adjusted based on amplification of the pixel signal; and
a compression unit configured to compress the digital data outputted from the A/D conversion unit.

2. The radiation detection apparatus according to claim 1, wherein the scintillator includes a cell type scintillator in which a plurality of scintillator cells is arranged in an array, each scintillator cell of the plurality of scintillator cells is isolated from each other by a barrier wall, and one or more pixels of the plurality of pixels are allocated to each scintillator cell of the plurality of scintillator cells.

3. The radiation detection apparatus according to claim 2, wherein two or more pixels of the plurality of pixels are allocated to each scintillator cell of the plurality of scintillator cells; and the compression unit is further configured to add the digital data of the two or more pixels allocated to each scintillator cell of the plurality of scintillator cells to compress the digital data.

4. The radiation detection apparatus according to claim 2, wherein two or more pixels of the plurality of pixels are allocated to each scintillator cell of the plurality of scintillator cells; and the compression unit is further configured to select a position of a pixel of the two or more pixels allocated to the scintillator cell as an incident position of the radiation, wherein the digital data of the pixel is maximum among the digital data of the two or more pixels allocated to the scintillator cell.

5. The radiation detection apparatus according to claim 2, wherein two or more pixels of the plurality of pixels are allocated to each scintillator cell of the plurality of scintillator cells; and the compression unit is further configured to:

add the digital data of the two or more pixels allocated to the scintillator cell;

compress the digital data based on the addition; and select a position of a pixel of the two or more pixels allocated to the scintillator cell as an incident position of the radiation, wherein the digital data of the pixel is maximum among the digital data of the two or more pixels allocated to the scintillator cell.

6. The radiation detection apparatus according to claim 1, further comprising a plurality of light detection blocks arranged in an array, wherein each light detection block of the plurality of light detection blocks includes the pixel substrate and the detection circuit substrate stacked with each other.

7. The radiation detection apparatus according to claim 6, wherein each detection block of the plurality of light detection blocks includes the compression unit.

8. The radiation detection apparatus according to claim 6, wherein the plurality of light detection blocks are on a first semiconductor substrate,
and
a plurality of pieces of the light detection blocks cut from the first semiconductor substrate are arranged in the array on a second semiconductor substrate.

9. The radiation detection apparatus according to claim 1, further comprising a radiation generation unit configured to generate the radiation, wherein the radiation generation unit is at a position that sandwiches a subject.

10. The radiation detection apparatus according to claim 1, wherein each pixel of the plurality of pixels has a photodiode (PD) having a substantially rectangular planar shape whose long side is equal to or longer than twice short side.

11. The radiation detection apparatus according to claim 10, wherein each pixel of the plurality of pixels has a plurality of PDs having the substantially rectangular planar shape whose long side is equal to longer than twice short side.

12. The radiation detection apparatus according to claim 1, wherein the quantization width of the A/D conversion is adjusted to one of a quantization width corresponding to the pixel signal of less than one electron or hole, or to a quantization width corresponding to the pixel signal of at least one electron or at least one hole.

13. The radiation detection apparatus according to claim 1, wherein the A/D conversion unit includes:

a comparator configured to:

compare a reference signal that changes with a specific inclination and the pixel signal with each other; and output a result of the comparison between the reference signal and the pixel signal; and a counter configured to:

count a period of time until a relationship in magnitude between the reference signal and the pixel signal reverses, based on the result of the comparison; and output a count value of the period of time, and the radiation detection apparatus further comprising an amplifier configured to amplify the pixel signal to be supplied to the comparator, wherein the amplifier has an adjustable gain, and the amplifier with the adjustable gain is provided as the adjustment mechanism.

14. The radiation detection apparatus according to claim 1, wherein the A/D conversion unit includes:

a comparator configured to:

compare a reference signal that changes with a specific inclination and the pixel signal with each other; and output a result of the comparison between the reference signal and the pixel signal; and a counter configured to:

count a period of time until a relationship in magnitude between the reference signal and the pixel signal reverses, based on the result of the comparison; and output a count value of the period of time, and the radiation detection apparatus further comprising a reference signal generation unit as the adjustment mechanism, wherein the reference signal generation unit is configured to:

generate the reference signal; and adjust the specific inclination of the reference signal to the quantization width of the A/D conversion.

15. The radiation detection apparatus according to claim 1, wherein the A/D conversion unit includes:

a comparator configured to:

compare a reference signal that changes with a specific inclination and the pixel signal with each other; and output a result of the comparison between the reference signal and the pixel signal; and a counter configured to:

count a period of time until a relationship in magnitude between the reference signal and the pixel signal reverses, based on the result of the comparison; and output a count value of the period of time, and a pixel of the plurality of pixels has, as the adjustment mechanism, a gain adjustment unit configured to adjust a gain of the pixel signal to be supplied to the comparator.

\* \* \* \* \*